United States Patent

Oono et al.

(10) Patent No.: US 6,723,483 B1
(45) Date of Patent: Apr. 20, 2004

(54) SULFONIUM SALT COMPOUNDS

(75) Inventors: Keiji Oono, Saitama (JP); Kazuhito Fukasawa, Saitama (JP); Kazunori Sakamoto, Saitama (JP); Fumiyoshi Urano, Saitama (JP); Motoshige Sumino, Saitama (JP); Shigeaki Imazeki, Saitama (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 74 days.

(21) Appl. No.: 09/730,744

(22) Filed: Dec. 7, 2000

(30) Foreign Application Priority Data

Dec. 27, 1999 (JP) .............................. 11-370655
Apr. 7, 2000 (JP) .......................... 2000-105789
Oct. 16, 2000 (JP) .......................... 2000-315061

(51) Int. Cl.[7] .......................... G03F 7/004; G03F 7/039; C07C 381/12
(52) U.S. Cl. .................... 430/170; 430/270.1; 430/905; 522/31; 568/18; 568/34; 568/35
(58) Field of Search .............................. 430/270.1, 905, 430/170; 522/31; 568/18, 34, 35

(56) References Cited

U.S. PATENT DOCUMENTS

| | | | |
|---|---|---|---|
| 5,500,453 A | * | 3/1996 | Toba et al. ............. 430/2 |
| 5,824,824 A | | 10/1998 | Osawa et al. |
| 5,844,057 A | | 12/1998 | Watanabe et al. |
| 5,847,218 A | | 12/1998 | Ohsawa et al. ............. 564/430 |
| 5,880,169 A | | 3/1999 | Osawa et al. |
| 6,022,665 A | | 2/2000 | Watanabe et al. |
| 6,027,854 A | | 2/2000 | Nishi et al. |
| 6,048,661 A | | 4/2000 | Nishi et al. |
| 6,060,213 A | | 5/2000 | Kodama |
| 6,106,993 A | | 8/2000 | Watanabe et al. |
| 6,111,143 A | * | 8/2000 | Park et al. ............... 568/18 |

FOREIGN PATENT DOCUMENTS

| | | |
|---|---|---|
| DE | 25 41 709 A | 4/1976 |
| EP | 0 898 201 A1 | 2/1999 |
| EP | 0 908 783 A1 | 4/1999 |
| EP | 0 989 459 A1 | 3/2000 |
| JP | 2296801 A | 12/1990 |
| JP | 3052815 A | 3/1991 |
| JP | 5255240 A | 10/1993 |
| JP | 6130669 A | 5/1994 |
| JP | 8245566 A | 9/1996 |
| JP | 8248626 A | 9/1996 |
| JP | 9012537 A | 1/1997 |
| JP | 9015848 A | 1/1997 |
| JP | 9160246 A | 6/1997 |

OTHER PUBLICATIONS

Database Chemabs 'Online, Chemical Abstracts Service, STN, Caplus accession No. 1994:232097, XP002162402 (abstract).

Database Chemabs 'Online, Chemical Abstracts Service, STN, Caplus accession No. 1997:178245, XP002162403 (abstract).

*Photo–CIDNP and Nanosecond Flash Photolysis on the Photodecomposition of Triarylsulfonium and Diarylhalonium Salts*, Polym. Material. Sci. Eng. (1981), pp. 181–184, Kevin M. Welsh et al.

*Polymeric Materials for Microelectronic Applications*, ACS Symposium Series 579 (1994), pp. 130–138, Hiroshi Ito et al.

*Reaction of Benzene with Diphenyl Sulfoxides*, Bull. Pharm. Chem. (1981), pp. 3753–3755, Yasuyuki Endo et al.

* cited by examiner

*Primary Examiner*—John S. Chu
(74) *Attorney, Agent, or Firm*—Armstrong, Kratz, Quintos, Hanson & Brooks, LLP

(57) ABSTRACT

A triphenyl sulfonium salt compound shown by the general formula [1] or [3].

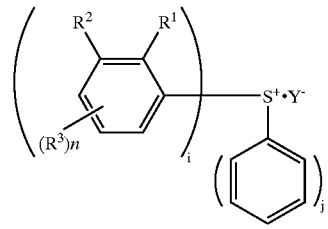

[1]

(wherein $R^1$ and $R^2$ are each independently a hydrogen atom or a lower alkyl group, provided that at least one of $R^1$ and $R^2$ are a lower alkyl group, $R^3$s are each independently an alkyl group, n is an integer of 0 to 3, i is an integer of 1 to 3, j is an integer of 0 to 2, provided that i+j=3, $Y^-$ is an anion derived from a sulfonic acid shown by the general formula [2]

$$R^4\text{—}SO_3H \qquad [2]$$

[wherein $R^4$ is an alkyl group or an aryl group which may have as a substituent an alkyl group]).

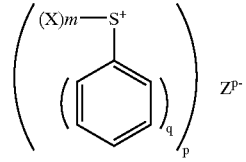

[3]

(wherein X is a phenyl group which has a substituent at an ortho- and/or a meta-position, m is an integer of 1 to 3, q is an integer of 0 to 2, provided that m+q=3, p is 1 or 2 and $Z^{p-}$ is an anion derived from a carboxylic acid).

34 Claims, No Drawings

SULFONIUM SALT COMPOUNDS

BACKGROUND OF THE INVENTION

The present invention relates to a sulfonium salt compound used as an acid generator and a photo polymerization initiator.

In accordance with the recent trend of higher density integration in semiconductor elements, wavelengths of light sources for irradiation instruments used in fine processing, particularly those used in lithography, become shorter and shorter, and in compliance with this trend, use has generally been made of chemically amplified resist compositions wherein an action of an acid generated from an acid generator as a photo sensitive compound is utilized. As the acid generators used in the chemically amplified resist compositions, onium salts such as sulfonium salts and iodonium salts, o-nitrobenzyl aryl sulfonate compounds, diazodisulfone compounds, disulfone compounds, dicarboxyimide sulfonate compounds, 2-acyloyl-2-aryl sulfonyl propane compounds, triaryl sulfonyloxybenzene compounds, and the like have been so far evaluated, and some of them have already been made into practical use, and even now further study has been conducted for the purpose of improvement thereof in compliance with rules and regulations for minimization.

Particularly the study for improvement has been focused on sulfonium salt compounds, among others, because they have been highlighted also as cationic type photo polymerization initiators.

Recently a proposal has been made on a process of combination use of aliphatic diazodisulfone compounds which generate weak acid upon being sensitized to radioactive rays with onium salts which generate strong acid upon being sensitized to radioactive rays (e.g. JP-A-10-48826), but this process is accompanied with such a drawback that use of sulfonium salts, of which counter anion is an aryl sulfonate, etc. often causes plugging of a filter of a spin coator with fine particles which are formed during storage arid thus those fine particles are transcribed upon a pattern formation so that the planned circuit cannot be formed.

Further, when sulfonium salts having $SbF_6^-$, $AsF_6^-$, $PF_6^-$, $BF_4^-$, $CF_3SO_3^-$, etc. as a counter anion, among others, are used, there are observed such drawbacks that acids generated are of high volatile, a large dimension deviation and deformation is caused by Delay Time due to the strength of the acid, influence of vicinal effects is uncontrolled, and the like (e.g. JP-A-5-249682; JP-A-8-123032, etc.) and side walls of a pattern are rough, and therefore these sulfonium salts are not appropriate as an acid generator for a resist.

Still further, sulfonium salts, wherein an alkyl group is substituted by an ortho-position of an aromatic ring, such as diphenyl-o-methylphenylsulfonium triflate, diphenyl-o-ethylphenylsulfonium triflate, diphenyl-o-isopropylphenylsulfonium triflate and diphenyl-3,4-dimethylphenylsulfonium triflate have been also proposed (e.g. JP-A2-296801; JP-A-5-255240; JP-A-6-130669; K. M. Welsh et al., Polym. Mater. Sci. Eng., 1989, 61, 181; K. Maeda et al., ACS Symp. Ser. 1994, 512, 130; Y. Endo et al., Bull. Pharm. Chem., 1981, 29(12), 3753; etc.), but they are also sulfonium salts having a triflate group ($CF_3SO_3$—) as a counter anion and therefore the same problems as above have been observed.

Additionally, sulfonium salts, wherein an alkoxy group is substituted by an meta-position of an aromatic ring, such as diphenyl-m-tert-butoxyphenylsulfonium triflate, diphenyl-m-tert-butoxyphenylsulfonium pentafluorobenzenesulfonate, diphenyl-3,4-tert-butoxyphenylsulfonium triflate and diphenyl-3,4-di-tertbutoxyphenylsulfonium tosylate have been proposed(e.g. JP-A-9-12537; JP-A-9-15848; JP-A-9-211866; JP-A-10-7650, etc.), but use of a triflate group as a counter anion causes the same problem as above and use of a tosylate group and a pentafluorobenzenesulfonate group as a counter anion causes a poor solubility in a solvent for a resist and formation of fine particles during storage, and therefore these sulfonium salts are not a appropriate as an acid generator for a resist.

SUMMARY OF THE INVENTION

The present invention has been completed under such circumstances as mentioned above and the theme of the invention is to provide sulfonium salt compounds which can be used more practically as an acid generator for a resist and as a cationic type photo polymerization initiator.

The present invention provides the following.

(1) A compound, which is shown by the general formula [1]

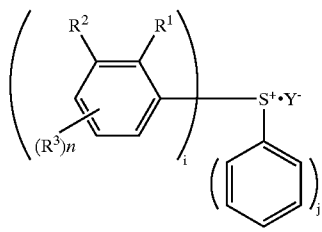

[1]

(wherein $R^1$ and $R^2$ are each independently a hydrogen atom or a lower alkyl group, provided that at least one of $R^1$ and $R^2$ are a lower alkyl group, $R^3$s are each independently an alkyl group, n is an integer of 0 to 3, i is an integer of 1 to 3, j is an integer of 0 to 2, provided that i+j=3, and $Y^-$ is an anion derived from an organic sulfonic acid of the general formula [2]

$$R^4\text{—}SO_3H \qquad [2]$$

[wherein $R^4$ is an alkyl group or an aryl group which may have an alkyl group as a substituent]).

(2) A compound, which is shown by the general formula [3]

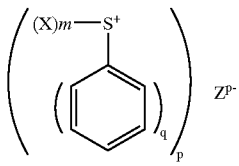

[3]

(wherein X is a phenyl group which has a substituent at an ortho- and/or a meta-position, m is an integer of 1 to 3, q is an integer of 0 to 2, provided that m+q=3, p is an integer of 1 or 2 and $Z^{p-}$ is an anion derived from an a carboxylic acid).

(3) An acid generator comprising the above compound.
(4) An acid generator composition comprising the above compound and a diazodisulfone compound.
(5) A resist composition comprising the above compound.
(6) A method for generation of an acid comprising irradiating the composition comprising the above compound with a light.

(7) A method for formation of a pattern comprising
  (i) a process of coating the above resist composition on a substrate,
  (ii) a process of irradiating, after heating, a light having a wavelength of 220 nm or less on the substrate through a mask, and
  (iii) a process of developing using a developing solution, after heat treatment, if necessary.
(8) A cationic type photo polymerization initiator comprising the above compound.
(9) A method for polymerization of an α,β-ethylenically unsaturated monomer comprising using the polymerization initiator in the above (8).

PREFERRED EMBODIMENTS OF THE INVENTION

The present inventors have conducted extensive study in order to realize the object mentioned above to arrive at the finding the compounds shown by the above general formula [1] and [3] act as an excellent acid generator for a resist or a cationic type photo polymerization initiator and finally the present invention has been accomplished on the basis of this finding.

In the general formula [1], the lower alkyl group shown by $R^1$ and $R^2$ may be straight chained, branched or cyclic and includes one having generally 1 to 6 carbon atoms, preferably 1 to 4 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, an isohexyl group, a sec-hexyl group, a tert-hexyl group, a 3-methylpentyl group, a 2-methylpentyl group, a 1,2-dimethylbutyl group, a cyclopropyl group, a cyclopentyl group, a cyclohexyl group, etc.

In the general formula [1], the alkyl group shown by $R^3$ may be straight chained, branched or cyclic and includes one having generally 1 to 10 carbon atoms, preferably 1 to 6 carbon atoms, which is specifically exemplified by the same as in the lower alkyl of $R^1$ and $R^2$, a n-heptyl group, an isoheptyl group, a n-octyl group, an isooctyl group, a n-nonyl group, a n-decyl group, a cycloheptyl group, a cyclooctyl group, a cyclononyl group, a cyclodecyl group, etc.

In the formula [2], the alkyl group shown by $R^4$ may be straight chained, branched or cyclic and includes one having generally 1 to 20 carbon atoms, preferably 6 to 12 carbon atoms, which are specifically exemplified by a methyl group, an ethyl group, a n-propyl group, an isopropyl group, a n-butyl group, an isobutyl group, a secbutyl group, a tert-butyl group, a n-pentyl group, an isopentyl group, a sec-pentyl group, a tert-pentyl group, a neopentyl group, a n-hexyl group, an isohexyl group, a 3-methylpentyl group, a 2-methylpentyl group, a 1,2-dimethylbutyl group, a n-heptyl group, an isoheptyl group, a sec-heptyl group, a n-octyl group, an isooctyl group, a secoctyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-icosyl group, a cyclopropyl group, a cyclopentyl group, a cyclohexyl group, a cycloheptyl group, a cyclooctyl group, a cyclononyl group, a cyclodecyl group, a cycloundecyl group, a cyclododecyl group, a cyclotetradecyl group, a cycloooctadecyl group, a cycloicosyl group, a bicyclo[2.1.0] pentyl group, a bicyclo[3.2.1]octyl group, a bicyclo[5.2.0] nonyl group, a tricyclo[5.3.1.1]dodecyl group, a perhydroanthryl group, a spiro[3.4]octyl group, a spiro[4,5]decyl group, etc.

In the general formula [2], the aryl group in the aryl group which may have an alkyl group as a substituent, shown by $R^4$ includes a phenyl group, a naphthyl group, an anthryl group, a pyrenyl group, etc. The alkyl group as a substituent of the above aryl group may be straight chained, branched or cyclic and includes one having generally 1 to 10 carbon atoms, preferably 1 to 6 carbon atoms, which are specifically exemplified by the same as in the alkyl group of $R^3$ and the alkyl group may be replaced by generally 1 to 5 hydrogen atoms, preferably 1 to 3 hydrogen atoms of the aryl group.

The specific examples of the compound shown by the general formula [2] are alkyl sulfonic acids such as ethanesulfonic acid, propanesulfonic acid, butanesulfonic acid, pentanesulfonic acid, hexanesulfonic acid, heptanesulfonic acid, octanesulfonic acid, nonanesulfonic acid, decanesulfonic acid, undecanesulfonic acid, dodecanesulfonic acid, tridecanesulfonic acid, tetradecanesulfonic acid, pentadecanesulfonic acid, hexadecanesulfonic acid, heptadecanesulfonic acid, octadecanesulfonic acid, nonadecanesulfonic acid, icosanesulfonic acid and cyclohexanesulfonic acid, aryl sulfonic acids such as benzenesulfonic acid, naphthalenesulfonic acid, anthracenesulfonic acid and p-toluenesulfonic acid, etc.

The preferable specific examples of the compound shown by the general formula [1] are diphenyl-o-methylphenylsulfonium p-toluenesulfonate, diphenyl-m-methylphenylsulfonium p-toluenesulfonate, diphenyl-2,4,6-trimethylphenylsulfonium p-toluenesulfonate, diphenyl-2,4-dimethylphenylsulfonium p-toluenesulfonate, diphenyl-o-methylphenylsulfonium benzenesulfonate, diphenyl-o-ethylphenylsulfonium p-toluenesulfonate, diphenyl-o-methylphenylsulfonium 1-naphthalenesulfonate, diphenyl-2,4,6-trimethylphenylsulfonium 1-naphthalenesulfonate, diphenyl-o-methylphenylsulfonium 4-ethylbenzenesulfonate, diphenyl-o-methylphenylsulfonium dodecylbenzenesulfonate, etc.

In the general formula [3], the substituent of the phenyl group having a substituent at an ortho-position and/or a meta-position, shown by X includes one shown by the general formula [6], [7], [8] and [9]

$$—R^7 \qquad [6]$$

$$—O—R^8 \qquad [7]$$

$$—S—R^9 \qquad [8]$$

(wherein $R^7$, $R^8$ and $R^9$ are each independently a halogen atom, an alkyl group which may have a substituent, an aryl group which may have a substituent or an aralkyl group which may have a substituent, $R^{10}$ and $R^9$ are each independently a halogen atom, an alkyl group which may have a substituent, an aryl group which may have a substituent, an aralkyl group which may have a substituent or an acyl group, and $R^{10}$ and $R^{11}$ may form a hetero ring together with a nitrogen atom to which they are bound).

In the general formula [6] to [9], the halogen atom shown by $R^7$, $R^8$, $R^9$, $R^{10}$ and $R^{11}$ includes a chlorine atom, a bromine atom, a fluorine atom and an iodine atom.

The alkyl group in the alkyl group which may have a substituent, shown by $R^7$, $R^8$, $R^9$, $R^{10}$ and $R^9$ may be straight chained, branched or cyclic and includes one having generally 1 to 6 carbon atoms, preferably 1 to 4 carbon atoms, which are specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a 3-methylpentyl group, a 2-methylpentyl group, a 1,2-dimethylbutyl group, a cyclopropyl group, a cyclopentyl group, a cyclohexyl group, etc. The substituent includes a halogen atom such as a chlorine atom, a bromine atom, a fluorine atom and an iodine atom, an amino group, a hydroxy group, etc.

The aryl group in the aryl group which may have a substituent, includes a phenyl group, a naphthyl group, an anthryl group, a pyrenyl group, etc.

The substituent in the aryl group includes a lower alkyl group such as a methyl group, an ethyl group, a propyl group and a butyl group, a halogen atom such as a chlorine atom, a bromine atom, a fluorine atom and an iodine atom, a lower alkoxy group such as a methoxy group, an ethoxy group and a propoxy group, a hydroxy group, an amino group, a nitro group, etc.

The hetero ring which may form by $R^{10}$, $R^{11}$ and a nitrogen atom to which they are bound includes a pyridine ring, a pyrrole ring, a pyrrolidine ring, a pyrroline ring, a piperidine ring, a quinoline ring, an indole ring, an isoindoline ring, a carbazole ring, etc.

The aralkyl group in the aralkyl group which may have a substituent, shown by $R^7$, $R^8$, $R^9$, $R^{10}$ and $R^{11}$ includes one having generally 7 to 10 carbon atoms, which is specifically exemplified by a benzyl group, a phenethyl group, a phenylpropyl group, etc.

The substituent in the aralkyl group includes the same as in the above substituent of the aryl group.

The acyl group shown by $R^{10}$ and $R^{11}$ includes one having generally 2 to 7 carbon atoms which is derived from an aliphatic carboxylic acid, which is specifically exemplified by an acetyl group, a propionyl group, a butyryl group, a valeryl group, a hexanoyl group, a heptanoyl group, etc.

In the general formula [3], an anion originated from a carboxylic acid, shown by $Z^{p-}$, includes one derived by a carboxylic acid shown by the general formula [4]

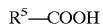
$R^5$—COOH [4]

(wherein $R^5$ is a hydrogen atom or a monovalent hydrocarbon residue which may have a substituent) or a dicarboxylic acid shown by the general formula [5]

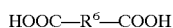
HOOC—$R^6$—COOH [5]

(wherein $R^6$ is a direct-linkage or a divalent hydrocarbon residue which may have a substituent).

In the general formula [4], a hydrocarbon residue in a monovalent hydrocarbon residue which may have a substituent, shown by $R^5$ includes an aliphatic hydrocarbon group, an aromatic hydrocarbon group and an aromatic aliphatic hydrocarbon group and the residue may have a sulfur atom in its chain.

The aliphatic hydrocarbon group includes an alkyl group, an alkenyl group, etc.

The alkyl group may be straight chained, branched or cyclic and includes one having generally 1 to 20, preferably 6 to 12 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a 3-methylpentyl group, a 2-methylpentyl group, a 1,2-dimethylbutyl group, a n-heptyl group, an isoheptyl group, a sec-heptyl group, a n-octyl group, an isooctyl group, a sec-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-icosyl group, a cyclopropyl group, a cyclopentyl group, a cyclohexyl group, a cycloheptyl group, a cyclooctyl group, a cyclodecyl group, a cycloundecyl group, a cyclododecyl group, a cyclotetradecyl group, a cyclooctadecyl group, a cycloicosyl group, etc.

The alkenyl group may be straight chained, branched or cyclic and includes one having generally 2 to 20 carbon atoms, preferably 6 to 12 carbon atoms, which is specifically exemplified by a vinyl group, an allyl group, a 1-propenyl group, an isopropenyl group, a 3-butenyl group, a 2-butenyl group, a 1-butenyl group, a 1,3-butadienyl group, a 4-pentenyl group, a 3-pentenyl group, a 2-pentenyl group, a 1-pentenyl group, a 1,3-pentadienyl group, a 2,4-pentadienyl group, a 1,1-dimethyl-2-propenyl group, a 1-ethyl-2-propenyl group, a 1,2-dimethyl-1-propenyl group, a 1-methyl-1-butenyl group, a 5-hexenyl group, a 4-hexenyl group, a 3-hexenyl group, a 2-hexenyl group, a 1-hexenyl group, a 1-methyl-1-hexenyl group, a 2-methyl-2-hexenyl group, a 3-methyl-1,3-hexadienyl group, a 1-heptenyl group, a 2-octenyl group, a 3-nonenyl group, a 4-decenyl group, a 1-undecenyl group, a 2-dodecenyl group, a 3-tridecenyl group, a 4-tetradecenyl group, a 5-pentadecenyl group, a 6-hexadecenyl group, a 7-heptadecenyl group, a 3-octadecenyl group, a 1-nonadecenyl group, a 2-icosadecenyl group, a 1-cyclopropenyl group, a 2-cyclopentenyl group, a 2,4-cyclopentandienyl group, a 1-cyclohexenyl group, a 2-cyclohexenyl group, a 3-cyclohexenyl group, a 2-cycloheptenyl group, a 2-cyclononenyl group, a 3-cyclododecenyl group, a 3-cyclopentadecenyl group, a 2-cyclooctadecenyl group, a 2-cycloicosenyl group, etc.

The aromatic hydrocarbon group includes an aryl group, etc. The aryl group includes one having generally 6 to 20 carbon atoms, preferably 6 to 14 carbon atoms, which is specifically exemplified by a phenyl group, a naphthyl group, an anthryl group, a 1-pyrenyl group, a perilenyl group, etc.

The aromatic aliphatic hydrocarbon group includes an aralkyl group. The aralkyl group includes one replacing the hydrogen atom of the above alkyl group by an aromatic ring, generally having 7 to 13 carbon atoms, preferably 7 to 10 carbon atoms, which is specifically exemplified by a benzyl group, a phenethyl group, a phenylpropyl group, a phenylbutyl group, a phenylpentyl group, a phenylhexyl group, a phenyl-1-methylhexyl group, a phenyl-3-cyclopentyl group, etc.

The substituent in the monovalent hydrocarbon residue which may have a substituent, shown by $R^5$ includes a halogen atom such as a chlorine atom, a fluorine atom, a bromine atom and in iodine atom, a lower alkyl group such as a methyl group, an ethyl group, a n-propyl group, an isopropyl group, a n-butyl group, an isobutyl group, a sec-butyl group and a tert-butyl group, a lower haloalkyl group such as a fluoromethyl group, a difluoromethyl group, a trifluoromethyl group, a bromomethyl group, a tribromomethyl group, a chloromethyl group, a dichloromethyl group, a trichloromethyl group, a trifluoroethyl group, a tribromoethyl group, a trichloroethyl group, a pentafluoroethyl group, a pentabromoethyl group, a pentachloroethyl group, a heptafluoropropyl group, a heptabromopropyl group and a heptacholoropropyl group, a lower alkoxy group such as a methoxy group, an ethoxy group, a propoxy group and a butoxy group, an amino group, a nitro group, an oxo group, a hydroxy group, a heterocyclic group, an aldehyde group, etc. and particularly a group having a electron-accepting such as a halogen atom, a lower haloalkyl group, an alkyl group and a nitro group is preferable.

The heterocyclic group includes 5- to 6-membered one containing a nitrogen atom, a sulfur atom and/or an oxygen atom as a 1 to 3 hetero atoms, which is specifically exemplified by a heterocyclic aliphatic group such as a 2-tetrahydrofuryl group, a 2-tetrahydrothienyl group, a 1-pyrrolidinyl group, a 2-pyrrolidinyl group, a 4-piperidinyl group and a 2-morpholinyl group, a heterocyclic aromatic group such as a 2-furyl group, a 2-thienyl group, a 1-pyrrolyl group, a 2-pyridyl group, a 3-pyridyl group, an isobenzofuranyl group, a chromenyl group, a 2H-pyrrolyl group, an imidazolyl group, a pyrazolyl group, a 5-pyrazolyl group, an indolizinyl group, an isoindolyl group, a 3H-indolyl group, an indolyl group, a 3-indolyl group, a 1H-indazolyl group and purinyl group, etc.

Specific examples of the compound shown by the general formula [4] are aliphatic saturated monocarboxylic acids such as acetic acid, propionic acid, butyric acid, isobutyric acid, valeric acid, isovaleric acid, pivalic acid, pentanoic acid, hexanoic acid, heptanoic acid, octanoic acid, nonanoic acid, decanoic acid, undecanoic acid, lauric acid, myristic acid, pentadecanoic acid, palmitic acid, heptadecanoic acid, stearic acid, nonadecanoic acid and icosanoic acid, aliphatic cyclic monocarboxylic acids such as cyclohexyl carboxylic acid, halogenated alkyl monocarboxylic acids such as fluoroacetic acid, trifluoroacetic acid, chloroacetic acid, dichloroacetic acid, trichloroacetic acid, bromoacetic acid, iodoacetic acid, perfluoropropionic acid, perchloroheptanoic acid, perfluoroheptanoic acid, perfluorooctanoic acid, perfluorodecanoic acid, perfluorododecanoic acid, perfluoroicosanoic acid and perfluorotetracontanoic acid, aliphatic unsaturated monocarboxylic acids such as acrylic acid, propiolic acid, methacrylic acid, crotonic acid, isocrotonic acid, 4-hexenic acid, oleic acid and elaidic acid, alicyclic monocarboxylic acids such as camphoric acid and adamantanoic acid, aromatic monocarboxylic acids such as benzoic acid, naphthoic acid and anthracene carboxylic acid, alkyl aromatic monocarboxylic acids such as toluic acid, halogenated aromatic monocarboxylic acids such as fluorobenzoic acid, chlorobenzoic acid, bromobenzoic acid, difluorobenzoic acid, dichlorobenzoic acid, dibromobenzoic acid, trifluorobenzoic acid, trichlorobenzoic acid, tribromobenzoic acid, tetrafluorobenzoic acid, tetrachlorobenzoic acid, tetrabromobenzoic acid, pentafluorobenzoic acid, pentachlorobenzoic acid and pentabromobenzoic acid, halogenated alkyl aromatic monocarboxylic acids such as trifluoromethylbenzoic acid, trichloromethylbenzoic acid and bis(trifluoromethyl)benzoic acid, halogenated alkoxy aromatic monocarboxylic acids such as trifluoromethoxybenzoic acid and trichloromethoxybenzoic acid, nitro aromatic monocarboxylic acids such as trinitrobenzoic acid, aralkyl monocarboxylic acids such as 2-phenylpropanoic acid, aralkyl acids such as hydroatropic acid, aryl alkenyl acids such as cinnamic acid and atropic acid, hydroxy aliphatic monocarboxylic acids such as glycolic acid, lactic acid and glyceric acid, aromatic hydroxyalkyl monocarboxylic acids such as benzilic acid and tropic acid, hydroxy aromatic monocarboxylic acids such as salicylic acid, protocatechuic acid, gallic acid, anisic acid and vanillinic acid, aliphatic ketone monocarboxylic acids such as pyruvic acid and acetoacetic acid, amino acids such as alanine, arginine, asparagine, aspartic acid, cystein, cystine, glutamic acid, glutamine, glycine, histidine, isoleucine, leucine, lysine, methionine, phenylalanine, proline, serine, threonine, tryptophan, tyrosine and valine, heterocylic monocarboxylic acids such as nicotinic acid, isonicotinic acid, furan carboxylic acid, thiophene carboxylic acid and 1-pyrrole carboxylic acid, p-formyl phenylacetic acid, 6-(2-naphthyl) hexanoic acid, etc.

In the general formula [5], the divalent hydrocarbon residue in the divalent hydrocarbon residue which may have a substituent, shown by $R^6$ includes a divalent aliphatic hydrocarbon group, a divalent aromatic hydrocarbon group, and a divalent aromatic aliphatic hydrocarbon group.

The divalent aliphatic hydrocarbon group includes an alkylene group, an alkenylene group, etc.

The alkylene group may be straight chained, branched or cyclic and includes one having generally 1 to 10, preferably 1 to 6, which is specifically exemplified by a methylene group, an ethylene group, a trimethylene group, a propylene group, a tetramethylene group, a butylene group, a 2-methylpropylene group, a pentamethylene group, a pentylene group, a 2-methyltetramethylene group, a 2,2-dimethyltrimethylene group, a 2-ethyltrimethylene group, a hexamethylene group, a hexylene group, a 2-methylpentamethylene group, a 3-methylpentamethylene group, a heptamethylene group, a heptylene group, an octamethylene group, an octylene group, a 2-ethylhexylene group, a nonamethylene group, a nonylene group, a decamethylene group, a decylene group, a cyclopropylene group, a cyclopentylene group, a cyclohexylene group, a cycloheptylene group, a cyclooctylene group, a cyclononylene group, a cyclodecylene group, etc.

The alkenylene group may be straight chained, branched or cyclic and includes one having generally 2 to 10 carbon atoms, preferably 2 to 6 carbon atoms, which is specifically exemplified by a vinylene group, a propenylene group, a 1-butenylene group, a 2-butenylene group, a 1-pentenylene group, a 2-pentenylene group, a 2-methyl-1-propenylene group, a 2-methyl-1-butenylene group, a 1-methyl-1-butenylene group, a 1-hexenylene group, a 2-hexenylene group, a 3-hexenylene group, a 1-heptenylene group, a 2-heptenylene group, a 3-heptenylene group, a 1-octenylene group, a 2-octenylene group, a 3-octenylene group, a 4-propyl-2-pentenylene group, a 1-nonenylene group, a 2-nonenylene group, a 1-decenylene group, a 4-cyclopenten-1,3-ylene group, a 3-cyclohexene-1,2-ylene group, etc.

The divalent aromatic hydrocarbon group includes an arylene group.

The arylene group includes one having generally 6 to 11 carbon atoms, which is specifically exemplified by an o-phenylene group, a m-phenylene group, a p-phenylene group, a 1,5-naphthylene group, a 1,8-naphthylene group, a 2,7-naphthylene group, a 2,6-naphthylene group, etc.

The divalent aromatic aliphatic hydrocarbon group includes one having generally 7 to 12 carbon atoms, which is specifically exemplified by —$CH_2$—$C_6H_4$—, —$C_2H_4$—$C_6H_4$—, —$CH(CH_3)$—$CH_6H_4$—, —$CH_2$—$C_6H_4$—$CH_2$—, —$CH(CH_3)$—$C_6H_4$—$C_2H_4$—, —$C_3H_6$—$C_6H_4$—$CH_2$—, —$C_3H_6$—$C_6H_4$—$C_2H_4$—, —$C_3H_6$—$C_6H_4$—$C_3H_6$—, —$CH_2CH(CH_3)$—$C_6H_4$—$C_2H_4$—, etc.

The substituent in the divalent hydrocarbon group which may have a substituent, shown by $R^6$ includes the same as the above substituent in the monovalent hydrocarbon group which may have a substituent shown by $R^5$.

Specific examples of the compound shown by the general formula [5] are aliphatic saturated dicarboxylic acids such as oxalic acid, malonic acid, succinic acid, glutaric acid, adipic acid, pimelic acid, suberic acid, azelaic acid and sebacic acid, aliphatic unsaturated dicarboxylic acids such as 4-propyl-2-pentene dicarboxylic acid, maleic acid, fumaric acid, citraconic acid and mesaconic acid, aromatic dicarboxylic acids such as phthalic acid, isophthalic acid, terephthalic acid and 1,5-naphthalene dicarboxylic acid, hydroxy aliphatic dicarboxylic acids such as tartronic acid, malic acid and tartaric acid, amino acids such as aspartic acid, cystine and glutamic acid, heterocyclic dicarboxylic acids such as 2,3-quinoline diacetic acid, etc.

Preferable specific examples of the compound shown by the general formula [3] are diphenyl-2,4,6-trimethylphenylsulfonium 1-perfluorooctanoate, diphenyl-2,4,6-trimethylphenylsulfonium p-trifluoromethylbenzoate, etc.

The compound of the present invention shown by the general formula [1] and [3] can be synthesized, for example, by the method [A], [B] or [C] shown by the following scheme, etc.

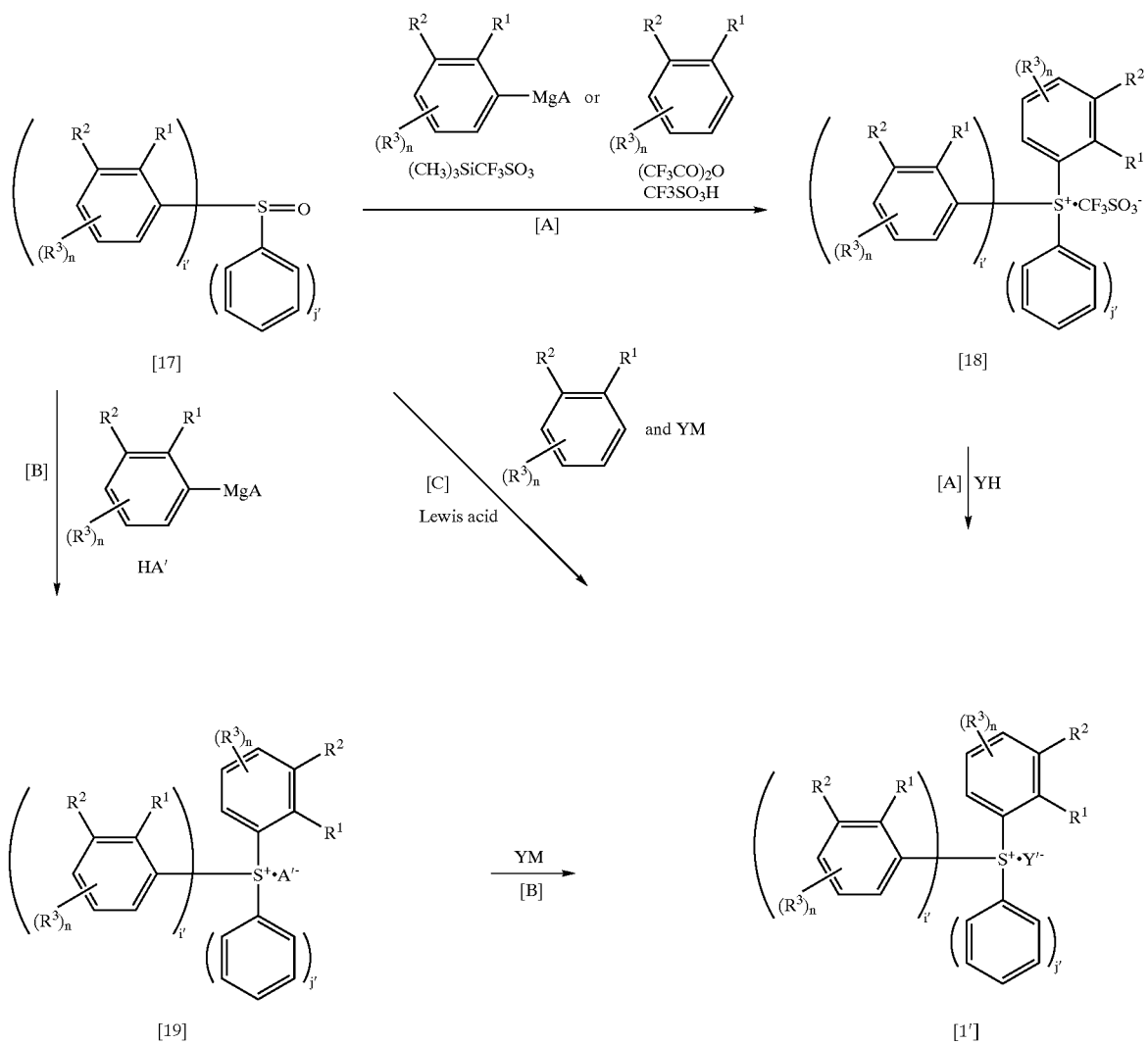

(wherein A and A' are each independently a halogen atom, M is a metal atom, $R^1$, $R^2$, $R^3$, Y and n have the same meaning as above, i' is an integer of 0 to 2 and j' is an integer of 0 to 2, providing that i'+j'=2).

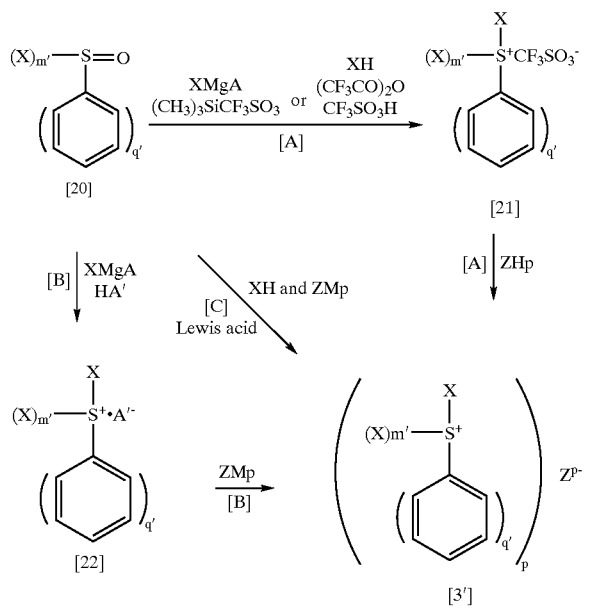

(wherein $Z^{p-}$, X, A, A', M and p have the same meaning as above, m' is an integer of 0 to 2 and q' is an integer of 0 to 2, providing that m'+q'=2).

The halogen atom shown by A and A' includes a chlorine atom, a fluorine atom, a bromine atom and an iodine atom.

The metal atom shown by M includes a silver atom, a lithium atom, a sodium atom, a potassium atom, a rubidium atom, a cesium atom, etc.

The Lewis acid includes $AlCl_3$, $AlBr_3$, $FeCl_3$, $ZnCl_3$, $SnCl_3$, $BF_3$, $Yb(OTf)_3$, $Se(OTf)_3$, etc.

Namely, in the method [A], the compound shown by the general formula [17] or [20] is dissolved in a halogenated hydrocarbon such as methylene chloride, methylene bromide, 1,2-dichloroethane and chloroform or a mixed solvent consisting of the halogenated hydrocarbon and an ether such as ethyl ether, isopropyl ether, tetrahydrofuran and 1,2-dimethoxy ethane, and trimethylsilyl trifluoromethanesulfonate in an amount of 0.8 to 2-mole parts and a Grignard reagent in an amount of 0.5 to 3 mole parts, relative to the compound shown by the general formula [17] or [20] are added thereto at −70 to −50° C. or a benzene derivative in an amount of 1 to 10 mole parts, trifluoroacetic anhydride in an amount of 1 to 3 mole parts and trifluoromethane sulfonic acid in an amount of 1 to 3 mole parts are added thereto at 0 to 30° C., followed by allowing a reaction to take place at 0 to 30° C. for 0.5 to 10 hours with stirring, whereby the compound shown by the general formula [18] or [21] is obtained. Thus obtained compound shown by the general formula [18] or [21] is dissolved in an aqueous solution of an alcohol such as methanol, ethanol and isopropanol and treated with an anion-exchange resin, and then 0.9 to 1.5 mole of a desired organic sulfonic acid or a desired organic carboxylic acid is added thereto. The resultant is, after removing an alcohol, dissolved again in an organic solvent such as methylene chloride, 1,2-dichloroethane, ethyl acetate, butyl acetate, propylene glycol monomethyl ether acetate, methyl isobutyl ketone and methyl ethyl ketone, followed by washing with water and concentrating under reduced pressure, whereby the compound of the present invention shown by the general formula [1'] or [3'] is obtained.

In the method [B], the compound shown by the general formula [17] or [20] is dissolved in a solvent such as a halogenated hydrocarbon including methylene chloride, methylene bromide, 1,2-dichloroethane, chloroform, etc. and an aromatic hydrocarbon including benzene, toluene, xylene, etc. or a mixed solvent consisting of the above solvent and an ether including ethyl ether, isopropyl ether, tetrahydrofuran, 1,2-dimethoxy ethane, etc., and a Grignard reagent in an amount of 0.5 to 3 mole parts relative to the compound shown by the general formula [17] or [20] is added thereto at −10 to 100° C., followed by allowing a reaction to take place at 0 to 100° C. for 0.5 to 10 hours with stirring. After the reaction, the reaction solution is treated with an aqueous solution of a hydrogen halide such as hydrogen bromide, hydrogen chloride and hydrogen iodide at 0 to 30° C., whereby the compound shown by the general formula [19] or [22] is obtained. The resulting compound is dissolved in methylene chloride, methanol, ethanol, isopropanol, water or a mixture thereof and 0.9 to 1.5 mole of a desired organic sulfonic acid salt or a desired organic carboxylic acid salt is added thereto, followed by allowing a reaction to take place at 0 to 50° C. for 0.5 to 20 hours with stirring, whereby the compound of the present invention shown by the general formula [1'] or [3'] is obtained.

In the method [C], the compound shown by the general formula [17] or [20] is reacted with a benzene derivative in an amount of 1 to 50 mole parts and a Lewis acid in an amount of 1 to 10 mole parts, relative to 1-mole part of the compound at −20 to 180° C. for 0.5 to 24 hours, with stirring and the resultant is further reacted with 1 to 5 mole parts of an organic sulfonic acid salt or an organic carboxylic acid salt at −20 to 100° C. for 0.5 to 24 hours with stirring, whereby the compound of the present invention shown by the general formula [1'] or [3'] is obtained.

The sulfonium salt of the present invention is useful as an acid generator comprised in a chemically amplified resist composition which has been used in the production of semiconductor elements and the salt can also show an excellent effect as a cationic type photo polymerization initiator.

<1>First, explanation is given concerning use of the sulfonium salt of the present invention as an acid generator for chemically amplified resist compositions.

The sulfonium salt of the present invention can be used alone as an acid generator, and more excellent effect can be expected by the use of the salt in combination with other kind of an acid generator. Particularly when the salt is used together with an acid generator capable of generating a weak acid and containing as a pending group an alkyl group, such as a diazodisulfone compound, the sulfonium salt of the present invention shows a remarkably excellent effect as an acid generator.

The diazodisulfone compound to be used together with the compound of the present invention includes one shown by the general formula [8]

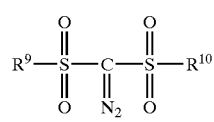

[8]

(wherein $R^9$ and $R^{10}$ are each independently an alkyl group).

In the general formula [8], the alkyl group shown by $R^9$ may be straight chained, branched or cyclic and includes one having generally 1 to 8 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a 3-methylpentyl group, a 2-methylpentyl group, a 1,2-dimethylbutyl group, a n-heptyl group, an isoheptyl group, a sec-heptyl group, a n-octyl group, an isooctyl group, a sec-octyl group, a cyclopropyl group, a cyclopentyl group, a cyclohexyl group, a cycloheptyl group, a cyclooctyl group, etc.

The alkyl group shown by $R^{10}$ are preferably branched or cyclic one and includes one having generally 3 to 8 carbon atoms, which is specifically exemplified by an isopropyl group, an isobutyl group, a sec-butyl group, a tert-butyl group, an isopentyl group, a sec-pentyl group, a tert-pentyl group, a neopentyl group, an isohexyl group, a 3-methylpentyl group, a 2-methylpentyl group, a 1,2-dimethylbutyl group, an isoheptyl group, a sec-heptyl group, an isooctyl group, a sec-octyl group, a cyclopropyl group, a cyclopentyl group, a cyclohexyl group, a cycloheptyl group, a cyclooctyl group, etc.

The specific examples of the diazodisulfone compound shown by the general formula [8] are bis (ethylsulfonyl) diazomethane, bis (1-methylethylsulfonyl) diazomethane, bis (1,1-dimethylethylsulfonyl) diazomethane, bis (cyclohexylsulfonyl) diazomethane, methylsulfonyl-1-methylethylsulfonyl diazomethane, methylsulfonyl-1,1-dimethylethylsulfonyl diazomethane, methylsulfonylcyclohexylsulfonyl diazomethane, ethylsulfonyl-1-methylethylsulfonyl diazomethane, ethylsulfonyl-1,1-dimethylethylsulfonyl diazomethane, ethylsulfonylcyclohexylsulfonyl diazomethane, bis (octanesulfonyl) diazomethane, methylethylsulfonyl-1,1-dimethylethylsulfonyl diazomethane, 1-methylethylsulfonylcyclohexylsulfonyl diazomethane, 1,1-dimethylethylsulfonylcyclohexylsulfonyl diazomethane, etc., and particularly when bis (1-methylethylsulfonyl) diazomethane, bis (1,1-dimethylethylsulfonyl) diazomethane, bis (cyclohexylsulfonyl) diazomethane, etc. are used together with the sulfonium salt of the present invention, prevention of generation of fine particles and various excellent properties as resists can be expected.

An amount of the sulfonium salt of the present invention to be used is, upon using alone, generally 0.1 to 10 wt %, preferably 0.5 to 5 wt %, and, upon using together with other kind of an acid generator, generally 0.05 to 5 wt %, preferably 0.1 to 3 wt %, while an amount of the other kind of the acid generator is generally 1 to 10 wt %, preferably 3 to 7 wt %, relative to the resin amount of the chemically amplified resist composition.

The sulfonium salt of the present invention can generate an acid by irradiation with not only deep UV and KrF excimer laser but also i-line, ArF excimer laser, $F_2$ laser (157 nm), electron beams and soft X-rays.

The chemically amplified positive tone resists to which the sulfonium salt of the present invention is applied are roughly classified into two component type resists and three component type resists.

The two component type resists comprise one or more kinds of polymers (or resins) containing as pending groups protecting groups which become soluble in an alkaline developing solution by an act of an acid, one or more kinds of the sulfonium salts of the present invention, if necessary, one or more kinds of acid generators except the above sulfonium salts, such as ones shown by the above general formula [8], and, upon necessity, basic compounds, acidic compounds, UV-absorbers, surfactants and solvents dissolving those components.

The three component type resists comprise one or more kinds of polymers (or resins) soluble in an alkaline developing solution, one or more kinds of dissolving-inhibiting agent s containing as pending groups protecting groups which become soluble in an alkaline developing solution by an act of an acid, one or more kinds of the sulfonium salts of the present invention, if necessary, one or more kinds of acid generators except the above sulfonium salts, such as ones shown by the above general formula [8], and, upon necessity, basic compounds, acidic compounds, UV-absorbers, surfactants, and solvents dissolving those components.

On the other hand, the chemically amplified negative tone resists of the present invention in which the sulfonium salts of the present invention are used comprise one or more kinds of polymers (or resins) soluble in an alkaline developing solution, cross-linking agents which cross-link polymers by heating in the presence of an acid so as to make the polymers insoluble in an alkaline developing solution, one or more kinds of the sulfonium salts of the present invention, if necessary, one or more kinds of acid generators except the above sulfonium salts, such as ones shown by the above general formula [8], and, upon necessity, basic compounds, acidic compounds, UV-absorbers, surfactants and solvents dissolving those components.

The polymers (or resins) containing as pending group protecting groups which become soluble in an alkaline developing solution by an act of an acid include those shown by the following general formula [9]

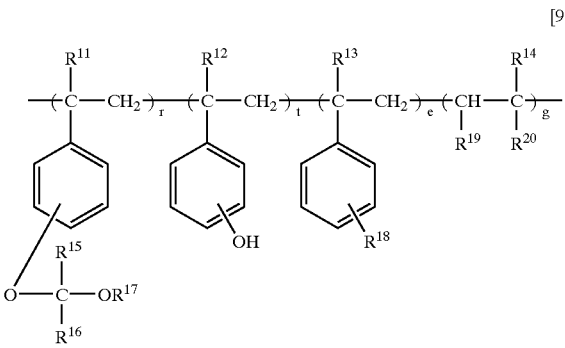

[9]

(wherein $R^{11}$, $R^{12}$, $R^{13}$ and $R^{14}$ are each independently a hydrogen atom or a methyl group, $R^{15}$ is a hydrogen atom or a lower alkyl group, $R^{16}$ is a lower alkyl group, and $R^{15}$ and $R^{16}$ may form an alicyclic ring together with a carbon atom to which they are bound, $R^{17}$ is an alkyl group or an aralkyl group, $R^{18}$ is a hydrogen atom, a lower alkyl group, a lower alkoxy group, a tetrahydropyranyloxy group, a tetrahydrofuranyloxy group, a tert-butoxycarbonyloxy group, a tert-amyloxycarbonyloxy group, a benzoyloxy group, an acetyloxy group, a pivaloyloxy group or a tert-butoxycarbonylmethyloxy group, $R^{19}$ is a hydrogen atom or a cyano group, $R^{20}$ is a cyano group or a carboxyl group which may be esterified, r, e and g are 0 or a natural number and t is a natural number, providing that $0 \leq r/r+t+e+g \leq 0.5$, $0 \leq e/r+t+e+g \leq 0.3$, $0 \leq g/r+t+e+g \leq 0.3$ and $0.2 < r+e+g/r+t+e+g \leq 0.8$).

In the general formula [9], the lower alkyl group shown by $R^{15}$, $R^{16}$ and $R^{18}$ may be straight chained, branched or cyclic and includes one having generally 1 to 6 carbons, which are specifically exemplified by a methyl group, an ethyl group, a n-propyl group, an isopropyl group, a n-butyl group, an isobutyl group, a tert-butyl group, a sec-butyl group, a n-pentyl group, an isopentyl group, a sec-pentyl group, a tert-pentyl group, a neopentyl group, a n-hexyl group, an isohexyl group, a sec-hexyl group, a tert-hexyl group, an 1-methylpentyl group, a 2-methylpentyl group, a 3-methylpentyl group, a cyclopropyl group, a cyclopentyl group, a cyclohexyl group, etc.

The alkyl group shown by $R^{17}$ may be straight chained, branched or cyclic and includes one having generally 1 to 10 carbons, which are specifically exemplified by a methyl group, an ethyl group, a n-propyl group, an isopropyl group, a n-butyl group, an isobutyl group, a tert-butyl group, a sec-butyl group, a n-pentyl group, an isopentyl group, a sec-pentyl group, a tert-pentyl group, a neopentyl group, a n-hexyl group, an isohexyl group, a sec-hexyl group, a tert-hexyl group, a 1-methylpentyl group, a 2-methylpentyl group, a 3-methylpentyl group, a n-heptyl group, an isoheptyl group, a sec-heptyl group, a tert-heptyl group, a 1-methylheptyl group, a 2-methylheptyl group, a 3-methylheptyl group, a 4-methylheptyl group, a n-octyl group, an isooctyl group, a tert-octyl group, a n-nonyl group, an isononyl group, a sec-nonyl group, a n-decyl group, an isodecyl group, a tert-decyl group, a cyclopropyl group, a cyclopentyl group, a cyclohexyl group, a cycloheptyl group, a cyclooctyl group, a cyclononyl group, a cyclodecyl group, etc.

The lower alkoxy group shown by $R^{18}$ may be straight chained, branched or cyclic and includes one having generally 1 to 6 carbon atoms, which are specifically exemplified by a methoxy group, an ethoxy group, a n-propoxy group, an isopropoxy group, a cyclopropoxy group, a n-butoxy group, an isobutoxy group, a tert-butoxy group, a sec-butoxy group, a n-pentyloxy group, an isopentyloxy group, a cyclopentyloxy group, a n-hexyloxy group, an isohexyloxy group, a cyclohexyloxy group, a 1-methylpentyloxy group, a 1-methylhexyloxy group, etc.

The carboxyl group which may be esterified, shown by $R^{20}$ includes one derived by substituting a part of the hydrogen atoms of the carboxyl group with an alkyl group, a bridged alicyclic hydrocarbon group, a mevalolactone group, etc.

The alkyl group may be straight chained, branched or cyclic and includes one having generally 1 to 8 carbons, which are specifically exemplified by a methyl group, an ethyl group, a n-propyl group, an isopropyl group, a cyclopropyl group, a n-butyl group, an isobutyl group, a tert-butyl group, a sec-butyl group, a n-pentyl group, an isopentyl group, a sec-pentyl group, a tert-pentyl group, a neopentyl group, a cyclopentyl group, a n-hexyl group, an isohexyl group, a sec-hexyl group, a tert-hexyl group, a 1-methylpentyl group, a cyclohexyl group, a n-heptyl group, an isoheptyl group, a sec-heptyl group, a tert-heptyl group, a cycloheptyl group, a n-octyl group, an isooctyl group, a sec-octyl group, a tert-octyl group, a cyclooctyl group, etc.

The bridged alicyclic hydrocarbon group includes one having generally 7 to 12 carbon atoms such as an isobornyl group, a norbornyl group, a 2-adamantyl group and a 2-methyl-2-adamantyl group.

The specific examples of the polymers shown by the general formula [9] are poly(p-1-ethoxyethoxystyrene/p-hydroxystyrene), poly(p-1-ethoxyethoxystyrene/p-hydroxystyrene/p-tert-butoxystyrene), poly(p-1-ethoxyethoxystyrene/p-hydroxystyrene/p-tert-butoxycarbonyloxystyrene), poly(p-1-ethoxyethoxystyrene/p-hydroxystyrene/p-tetrahydropyranyloxystyrene), poly(p-1-ethoxyethoxystyrene/p-hydroxystyrene/p-tert-butoxycarbonylmethyloxystyrene), poly(p-1-ethoxyethoxystyrene/p-hydroxystyrene/p-isopropoxystyrene), poly(p-1-ethoxyethoxystyrene/p-hydroxystyrene/p-benzoyloxystyrene), poly(p-1-ethoxyethoxystyrene/p-hydroxystyrene/p-pivaloyloxystyrene), poly(p-1-ethoxyethoxystyrene/p-hydroxystyrene/tert-butylacrylate), poly(p-1-ethoxyethoxystyrene/p-hydroxystyrene/2-adamantylacrylate), poly(p-1-ethoxyethoxystyrene/p-hydroxystyrene/isobomnylacrylate), poly(p-1-ethoxyethoxystyrene/p-hydroxystyrene/cyclohexylacrylate), poly(p-1-ethoxyethoxystyrene/p-hydroxystyrene/methylmethacrylate), poly(p-1-ethoxyethoxystyrene/p-hydroxystyrene/styrene/tert-butylacrylate), poly(p-1-ethoxyethoxystyrene/p-hydroxystyrene/styrene/tert-amylacrylate), poly(p-1-ethoxyethoxystyrene/p-hydroxystyrene/styrene/1-methylcyclohexylacrylate), poly(p-1-ethoxyethoxystyrene/p-hydroxystyrene/styrene/mevalotactoneacrylate), poly(p-1-ethoxypropoxystyrene/p-hydroxystyrene), poly(p-1-ethoxypropoxystyrene/p-hydroxystyrene/p-tert-butoxystyrene), poly(p-1-ethoxypropoxystyrene/p-hydroxystyrene/p-tert-butoxycarbonyloxystyrene), poly(p-1-ethoxypropoxystyrene/p-hydroxystyrene/p-tetrahydropyranyloxystyrene), poly(p-1-isobutoxyethoxystyrene/p-hydroxystyrene), poly(p-1-cyclohexyloxyethoxystyrene/p-hydroxystyrene), poly(p-1-cyclohexyloxyethoxystyrene/p-hydroxystyrene/p-tert-butoxystyrene), poly(p-1-cyclohexyloxyethoxystyrene/p-hydroxystyrene/p-tert-butoxycarbonyloxystyrene), poly(p-1-cyclohexyloxyethoxystyrene/p-hydroxystyrene/p-tetrahydropyranyloxystyrene), poly(p-tert-butoxystyrene/p-hydroxystyrene), poly(p-tert-butoxycarbonyloxystyrene/p-hydroxystyrene), poly(p-tetrahydropyranyloxystyrene/p-hydroxystyrene), poly(phydroxystyrene/styrene/tert-butylacrylate), poly(p-hydroxystyrene/styrene/tert-amylacrylate), poly(p-hydroxystyrene/styrene/1-methylcyclohexylacrylate), poly(p-hydroxystyrene/styrene/mevalolactoneacrylate), poly(p-hydroxystyrene/styrene/2-methyl-2-adamantylacrylate), poly(p-1-octyloxyethoxystyrene/p-hydroxystyrene/pacetyloxystyrene), poly(p-1-benzyloxyethoxystyrene/p-hydroxystyrene/pacetyloxystyrene), poly[p-1-(3-cyclobenzylpropyl)oxyethoxystyrene/p-hydroxystyrene/p-tert-butoxycarbonyloxystyrene], poly(p-1-ethoxyethoxystyrene/p-hydroxystyrene/p-acetyloxystyrene), etc. Those polymers may be used alone or in a suitable combination of two or more thereof.

A weight average molecular weight (Mw) of the polymer shown by the general formula [9] is generally 3,000 to 50,000, preferably 5,000 to 25,000, more preferably 5,000 to 20,000.

A dispersion (Mw/Mn) of the polymer shown by the general formula [9] is generally 1.0 to 3.5, preferably 1.0 to 2.5, more preferably 1.0 to 1.5.

The polymer (or resin) soluble in an alkaline developing solution includes one shown by the following general formula [10]

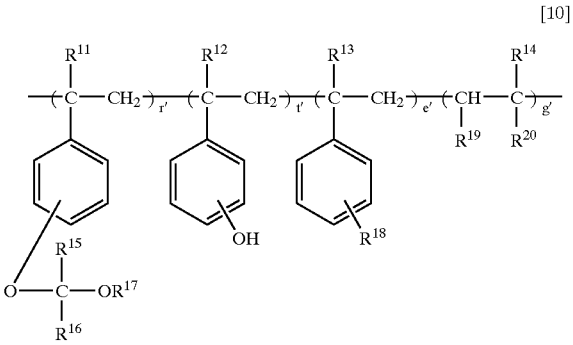

[10]

(wherein r', e' and g' are 0 or a natural number, t' is a natural number, providing that $0 \leq r'/r'+t'+e'+g' \leq 0.2$, $0 \leq e'/r'+t'+e'+g' \leq 0.2$, $0 \leq g'/r'+t'+e'+g' \leq 0.2$ and $0 \leq r'+e'+g'/r'+t'+e'+g' \leq 0.2$, and $R^{11}$, $R^{12}$, $R^{13}$, $R^{14}$, $R^{15}$, $R^{16}$, $R^{17}$, $R^{18}$, $R^{19}$ and $R^{20}$ have the same meaning as above).

The specific examples of the polymers shown by the general formula [10] are poly(p-hydroxystyrene), poly(p-1-ethoxyethoxystyrene/p-hydroxystyrene), poly(p-1-ethoxyethoxystyrene/p-hydroxystyrene/p-tert-butoxystyrene), poly(p-1-ethoxyethoxystyrene/p-hydroxystyrene/p-tert-butoxycarbonyloxystyrene), poly(p-

1-ethoxypropoxystyrene/p-hydroxystyrene), poly(p-1-isobutoxyethoxystyrene/p-hydroxystyrene), poly(p-1-cyclohexyloxyethoxystyrene/p-hydroxystyrene), poly(p-tert-butoxystyrene/p-hydroxystyrene), poly(p-tert-butoxycarbonyloxystyrene/p-hydroxystyrene), poly(p-tetrahydropyranyloxystyrene/p-hydroxystyrene), poly(p-hydroxystyrene/styrene/tert-butylacrylate), poly(p-hydroxystyrene/styrene/tert-amylacrylate), etc.

A ratio of the p-hydroxystyrene unit in the above copolymer is not less than 80 mole %.

A weight-average molecular weight (Mw) of the polymer shown by the general formula [10] to be used in the three component chemically amplified positive tone resist is generally 3,000 to 50,000, preferably 5,000 to 25,000, more preferably 5,000 to 20,000, and dispersion (Mw/Mn) is generally 1.0 to 3.5, preferably 1.0 to 2.5, more preferably 1.0 to 1.5.

A weight-average molecular weight (Mw) of the polymer shown by the general formula [10] to be used in the chemically amplified negative tone resist is generally 1,000 to 30,000, preferably 1,500 to 10,000, more preferably 2,000 to 5,000, and dispersion (Mw/Mn) is generally 1.0 to 2.5, preferably 1.0 to 1.5.

The dissolving-inhibiting agent containing as a pending group a protecting group which becomes soluble in an alkaline developing solution by an act of an acid includes compounds shown by the following general formula [11], [12] or [13]

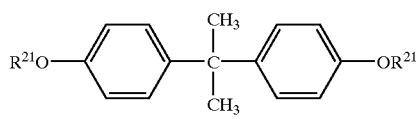

[11]

(wherein $R^{21}$s are each independently an acid labile group).

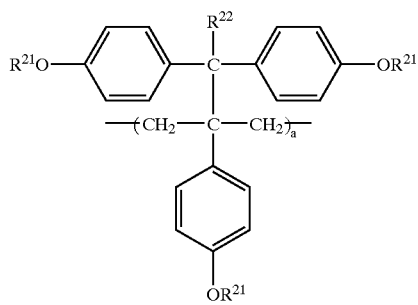

[12]

(wherein $R^{22}$ is a hydrogen atom or a methyl group, a is a natural number and $R^{21}$ has the same meaning as above).

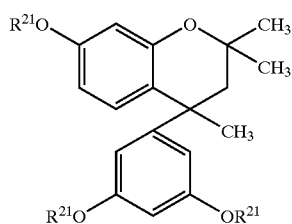

[13]

(wherein $R^{21}$ has the same meaning as above).

The acid labile group shown by $R^{21}$ in the general formula [11], [12] and [13] includes a tert-butoxycarbonyl group, a tert-amyloxycarbonyl group, a tetrahydropyranyl group, a tert-butyl group, a tert-amyl group, a 1-ethoxyethyl group, a 1-ethylpropyl group, a 1-cyclohexyloxyethyl group, a 1-isobutyloxyethyl group, etc.

The specific examples of the dissolving-inhibiting agent shown by the general formula [11] are 2,2-bis(p-tert-butoxyphenyl)propane, 2,2-bis(p-tert-butoxycarbonyloxyphenyl)propane, 2,2-bis(p-tetrahydropyranyloxyphenyl) propane, 2,2-bis(p-1-ethoxyethoxyphenyl)propane, 2,2-bis(p-1-cyclohexyloxyethoxyphenyl)propane, 2,2-bis(p-1-isobutoxyethoxyphenyl)propane, etc.

The specific examples of the dissolving-inhibiting agent shown by the general formula [12] are tris(p-tert-butoxyphenyl)methane, tris(p-tertbutoxycarbonyloxyphenyl)methane, tris(p-tetrahydropyranyloxyphenyl) methane, tris(p-1-ethoxyethoxyphenyl)methane, tris(p-1-cyclohexyloxyethoxyphenyl)methane, tris(p-1-isobutoxyethoxyphenyl)methane, 1,1,1-tris(p-tert-butoxyphenyl)ethane, 1,1,1-tris(p-tert-butoxycarbonyloxyphenyl)ethane, 1,1,1-tris(p-tetrahydropyranyloxyphenyl) ethane, 1,1,1-tris(p-1-ethoxyethoxyphenyl)ethane, 1,1,1-tris(p-icyclohexyloxyethoxyphenyl)ethane, 1,1,1-tris(p-1-isobutoxyethoxyphenyl)ethane, 2,2,3-tris(p-tert-butoxyphenyl)-2-methylbutane, 2,2,3-tris(p-tertbutoxycarbonyloxyphenyl)-2-methylbutane, 2,2,3-tris(p-tetrahydropyranyloxyphenyl)-2-methylbutane, 2,2,3-tris(p-1-ethoxyethoxyphenyl)-2-methylbutane, 2,2,3-tris(p-1-cyclohexyloxyethoxyphenyl)-2-methylbutane, 2,2,3-tris(p-1-isobutoxyethoxyphenyl)-2-methylbutane, etc.

The specific examples of the dissolving-inhibiting agent shown by the general formula [13] are 3,4-dihydro-4-(2,4-di-tert-butoxyphenyl)-7-(tert-butoxy)-2,2,4-trimethyl-2H-1-benzopyrane, 3,4-dihydro-4-(2,4-di-tert-butoxycarbonyl-oxyphenyl)-7(tert-butoxycarbonyloxy)-2,2,4-trimethyl-2H-1-benzopyrane, 3,4-dihydro-4-(2,4-ditetrahydropyranyloxy-phenyl)-7-(tetrahydropyranyloxy)-2,2,4-trimethyl-2H-1-benzpoyrane, 3,4-dihydro-4-[2,4-di-(1-ethoxyethoxy) phenyl]-7-(1-ethoxyethoxy)-2,2,4-trimethyl-2H-1-benzopyrane, 3,4-dihydro-4-[2,4-di-(1-cyclohexyloxy-ethoxy)phenyl]-7-(1-cyclohexyloxyethoxy)-2,2,4-trimethyl-2H-1-benzopyrane, 3,4-dihydro-4[2,4-di-(1-isobutoxyetoxy)phenyl]-7-(1-isobutoxyethoxy)-2,2,4-trimethyl-2H-1-benzopyrane, etc.

An amount of the dissolving-inhibiting agent shown by the general formula [11], [12] and/or [13] to be used in a three component chemically amplified positive tone resist is generally 5 to 30 wt %, preferably 15 to 25 wt %, relative to the total amount of the polymer.

An amount of the dissolving-inhibiting agent shown by the general formula [11], [12] and/or [13] to be used in a two component chemically amplified positive tone resist is generally 0.1 to 5 wt %, preferably 0.5 to 2 wt %, relative to the total amount of the polymer.

The cross-linking agent which cross-links the polymer to make it insoluble in an alkaline developing solution by treatment under heating in the presence of an acid includes one shown by the following general formula [14] or [15]

[14]

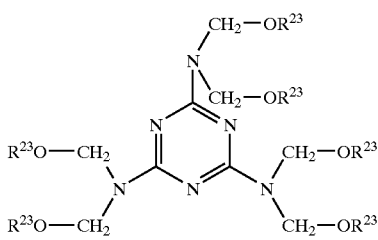

(wherein $R^{23}$s are each independently a hydrogen atom or a lower alkyl group).

[15]

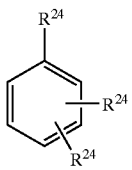

(wherein $R^{24}$s are each independently a hydrogen atom or a lower alkoxymethyl group).

The lower alkyl group shown by $R^{23}$ in the general formula [14] may be straight chained, branched or cyclic and includes one having generally 1 to 6 carbon atoms, which is specifically exemplified by a methyl group, an ethyl group, a n-propyl group, an isopropyl group, a cyclopropyl group, a n-butyl group, an isobutyl group, a sec-butyl group, a tert-butyl group, a n-pentyl group, an isopentyl group, a sec-pentyl group, a tert-pentyl group, a neopentyl group, a cyclopentyl group, a n-hexyl group, an isohexyl group, a sec-hexyl group, a tert-hexyl group, a 1-methylpentyl group, a 2-methylpentyl group, a cyclohexyl group, etc.

The alkoxy group in the lower alkoxymethyl group shown by $R^{24}$ in the general formula [15] may be straight chained, branched or cyclic and includes one having generally 1 to 6 carbon atoms, which is specifically exemplified by a methoxy group, an ethoxy group, a n-propoxy group, an isopropoxy group, a cyclopropoxy group, a n-butoxy group, an isobutoxy group, a tert-butoxy group, a sec-butoxy group, a n-pentyloxy group, an isopentyloxy group, a cyclopentyloxy group, a n-hexyloxy group, an isohexyoxy group, a cyclohexyloxy group, a 1-methylpentyloxy group, etc.

The specific examples of the cross-linking agent shown by the general formula [14] are 2,4,6-tris[1,3,5-bis(methoxymethyl)amino]-1,3,5-triazine, 2,4,6-tris[1,3,5-bis(ethoxymethyl)amino]-1,3,5-triazine, 2,4,6-tris[1,3,5-bis(isopropoxymethyl)amino]1,3,5-triazine, 2,4,6-tris[1,3,5-bis(tert-butoxymethyl)amino]-1,3,5-triazine, 2,4,6-tris[1,3,5-bis(cyclohexyloxymethyl)amino]-1,3,5-triazine, 2,4,6-tris(methoxymethylhydroxymethyl)amino-1,3,5-triazine, 2,4-bis[bis(methoxymethyl)amino]-6-methoxymethylhydroxymethylamino-1,3,5-triazine, etc.

The specific examples of the cross-linking agent shown by the general formula [15] are 1,2,3-tris(methoxymethyl)benzene, 1,2,3-tris(ethoxymethyl)benzene, 1,2,3-tris(isopropoxymethyl)benzene, 1,2,3-tris(tert-butoxy)benzene, 1,2,3-tris(cyclohexyloxymethyl)benzene, 1,2,4-tris(methoxymethyl)benzene, 1,2,4-tris(ethoxymethyl)benzene, 1,2,4-tris(isopropoxymethyl)benzene, 1,2,4-tris(tertbutoxymethyl)benzene, 1,2,4-tris(cyclohexyloxymethyl)benzene, 1,3,5-tris(methoxymethyl)benzene, 1,3,5-tris(ethoxymethyl)benzene, 1,3,5-tris(isopropoxymethyl)benzene, 1,3,5-tris(tert-butoxymethyl)benzene, 1,3,5-tris(cyclohexyloxymethyl)benzene, 1,2-bis(methoxymethyl)benzene, 1,2-bis(isopropoxymethyl)benzene, 1,2-bis(cyclohexyloxymethyl)benzene, 1,3-bis(methoxymethyl)benzene, 1,3-bis(isopropoxymethyl)benzene, 1,3-bis(cyclohexyloxymethyl)benzene, 1,4-bis(methoxymethyl)benzene, 1,4-bis(isopropoxymethyl)benzene, 1,4-bis(cyclohexyloxymethyl)benzene, etc.

An amount of the cross-linking agent shown by the general formula [14] and/or [15] to be used in a chemically amplified negative tone resist is generally 5 to 30 wt %, preferably 15 to 25 wt %, relative to the total amount of the polymer.

The basic compound to be used upon necessity includes pyridine, picoline, triethylamine, tri n-butylamine, tri n-octylamine, dioctylmethylamine, dicyclohexylmethylamine, N-methylpyrrolidine, N-methylpiperidine, triethanolamine, triisopropanolamine, dimethyldodecylamine, dimethylhexadecylamine, tribenzylamine, tris[2-(2-methoxyethoxy)ethyl]amine, tetramethylammonium hydroxide, tetraethylammonium hydroxide, tetra-n-butylammonium hydroxide, polyvinylpyridine, poly(vinylpyridine/methyl methacrylate), etc. Those compounds may be used alone or in a suitable combination of two or more thereof.

The acidic compound to be used upon necessity includes phthalic acid, succinic acid, malonic acid, salicylic acid, o-acetyl benzoic acid, o-nitro benzoic acid, thiosalicylic acid, diphenolic acid, succinimide, saccharin, ascorbic acid, etc.

The UV-absorber to be used upon necessity includes 9-diazofluorenone, 1-diazo-2-tetralone, 9-diazo-10-phenantholone, 2,2'-4,4'-tetrahydroxybenzophenone, 9-(2-methoxyethoxy)methylanthracene, 9-(2-ethoxyethoxy)methylanthracene, 9-(4-methoxybutoxy)methylanthracene, 9-anthracenemethylacetate, dihydroxyflavanone, quercetin, trihydroxyflavanone, 4,4'-dihydroxybenzophenone, etc.

The surfactant to be used upon necessity includes a fluorine-containing nonionic type such as Fluorad (a trade name of Sumitomo 3M, Ltd.), Surflon (a trade name of Asahi Glass Co., Ltd.), Unidyne (a trade name of Daikin Industries, Ltd.), Megafac (a trade name of Dainippon Ink & Chemicals, Incorp.) and Eftop (a trade name of Tohkem Products Corp.), polyethylene glycol, polypropylene glycol, polyoxyethylene cetyl ether, etc.

Amounts of the basic compound, the acidic compound, the UV-absorber and/or the surfactant, which are to be used upon necessity, are each generally 0.000001 to 1 wt %, preferably 0.00001 to 0.5 wt %, relative to the total amount of the polymer in all kinds of resists.

The solvent includes methyl cellosolve acetate, ethyl cellosolve acetate, propylene glycol monomethyl ether, propylene glycol monomethyl ether acetate, propylene glycol monoethyl ether acetate, methyl lactate, ethyl lactate, propyl lactate, 2-ethoxyethylacetate, methyl pyruvate, ethyl pyruvate, methyl 3-methoxypropionate, ethyl 3-methoxypropionate, N,N-dimethylformamide, N,N-dimethylacetamide, cyclohexanone, methylethyl ketone, 2-heptanone, β-propiolactone, β-butyrolactone, γ-butyrolactone, γ-valerolactone, δ-valerolactone, 1,4-dioxane, diethyleneglycol monomethyl ether, diethyleneglycol dimethyl ether, ethyleneglycol monoisopropyl ether, N-methyl-2-pyrrolidone, etc. Those solvents may be used alone or in a suitable combination of two or more thereof.

An amount of the solvent to be used in a chemically amplified resist is in all kinds of resists generally 3 to 10 wt parts, preferably 3 to 7 wt parts, relative to the total amount of the solid content of the resist.

For the purpose of realizing ultra-minimized processing such as resolution of 0.1 μm or less by irradiation with electron beams and $F_2$ excimer laser, resists for surface-resolution processes have also been proposed (JP-A-9-189998) in order to form a pattern by forming a thin membrane on an overcoat composed of novolac resin, etc., subjecting only this thin membrane to a chemically amplified reaction, and then conducting a silylation reaction and a plasma etching (dry etching), and the sulfonium salts of the present invention can be used in this kind of resist.

The resist for the surface-resolution process is used in a form of a diluted solution, and the ratios of an acid generator such as the sulfonium salts of the present invention, the basic compound, the surfactant, etc., which are to be used, may be the same as mentioned also in the case of the surface-resolution process. An amount of the solvent, however, is generally 15 to 40 wt parts, preferably 20 to 30 wt parts, relative to the total amount of the solid content in the resist.

The above mentioned chemically amplified negative tone resist can be used as it is also as the positive tone resist in the surface-resolution process (in the surface-resolution process, a negative tone resist is reversed to a positive one during a silylation step). An amount of the solvent to be used is generally 15 to 40 wt parts, preferably 20 to 30 wt parts, relative to the total amount of the solid content of the resist.

Further the positive tone resist can be used as it is also as the negative tone resist in the surface-resolution process (in the surface-resolution process, a positive tone resist is reversed to a negative one during a silylation step). An amount of the solvent to be used is generally 15 to 40 wt parts, preferably 20 to 30 wt parts, relative to the total amount of the solid content of the resist.

In the following is given concrete explanation concerning the role of the sulfonium salts of the present invention used as an acid generator in chemically amplified positive tone resists.

First, when the sulfonium salts of the present invention is irradiated with deep UV, KrF excimer laser, an acid is generated according to the photoreaction shown the following scheme;

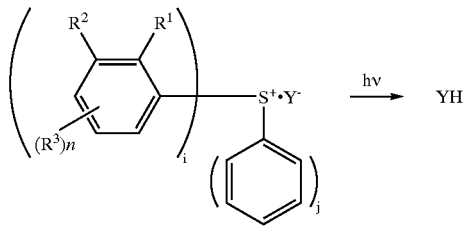

(wherein h v is a light and $R^1$, $R^2$, $R^3$, $Y^-$, n, i and j have the same meaning as above).

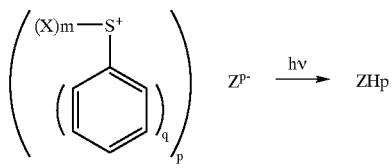

(wherein, X, $Z^{p-}$, m, q, p and h v have the same meaning as above).

By heating treatment after the exposure step, the protecting group of the phenolic hydroxy group is subjected to chemical change to convert into a phenolic hydroxy group by an act of an acid generated from the sulfonium salt as shown in the following scheme, whereby the polymer becomes alkaline soluble to dissolve out in a developing solution during a developing process;

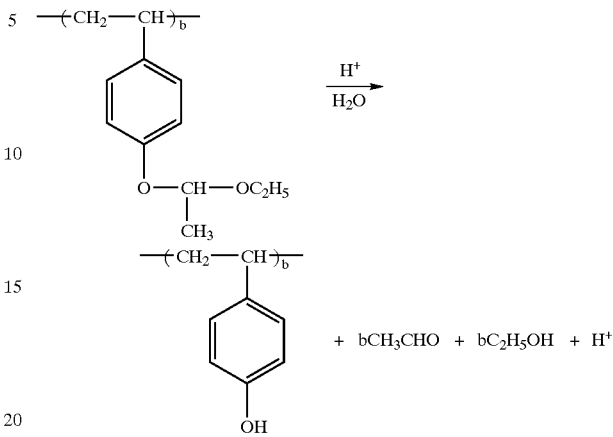

(wherein b is a natural number).

As the result, there is caused a large difference in the solubility in the alkaline developing solution between the exposure part and the non-exposure part wherein the above reaction is not caused, whereby a positive tone pattern having a good contrast is formed.

Further, in the sulfonium salts of the present invention, there is caused a large difference in an effect of preventing formation of fine particles which is the most important between p-alkyl substituted sulfonium salts having no alkyl group as a pending group at the o- or m-position (the counter anion is limited to an aromatic sulfonate which may have an alkyl group as a substituent) and those having an alkyl group as a pending group at the o- or m-position. This difference is assumed to be caused by difference in easiness of stereostructural cohesion of the compounds.

<2>Then explanation is given below concerning the use of the sulfonium salts of the present invention as a cationic photo polymerization initiator.

The sulfonium salts of the present invention generate an acid by irradiation with light. When a various kind of α,β-ethylenically unsaturated monomer exists in the system upon the irradiation, a polymerization reaction rapidly proceeds.

Polymerization or copolymerization of α,β-ethylenically unsaturated monomer by using the sulfonium salts of the present invention as a polymerization initiator can be conducted by allowing the monomer and the sulfonium salt to exist in the system in the presence of a suitable solvent or in the absence of the solvent under inert gas atmosphere if necessary after a conventional polymerization method.

The α,β-ethylenically unsaturated monomer includes one shown by the general formula [16]

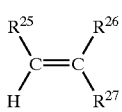

[16]

(wherein $R^{25}$ is a hydrogen atom, a lower alkyl group, a carboxyl group, a carboxyalkyl group, an alkyloxycarbonyl group, a cyano group or an aldehyde group, $R^{26}$ is a hydrogen atom, a lower alkyl group, a carboxyl group, an alkyloxycarbonyl group, a cyano group or a halogen atom, $R^{27}$ is a hydrogen atom, a lower alkyl group, a haloalkyl group, an aryl group which may have a substituent, an aliphatic heterocyclic group, an aromatic heterocyclic group, a halogen atom, an alkyloxycarbonyl group, a cyano group, a cyano-containing alkyl group, an acyloxy group, a carboxyl group, a carboxyalkyl group, an aldehyde group, a carbamoyl group or a n-alkylcarbamoyl group, and $R^{25}$ and $R^{26}$ may form an alicyclic ring together with the adjacent —C=C— group).

The lower alkyl group shown by $R^{25}$ to $R^{27}$ in the general formula [16] may be straight chained, branched or cyclic and includes one having 1 to 6 carbon atoms, which is specifically exemplified by a methyl group, an ethyl group, a n-propyl group, an isopropyl group, a n-butyl group, an isobutyl group, a tert-butyl group, a sec-butyl group, a n-pentyl group, an isopentyl group, a tert-pentyl group, a 1-methylpentyl group, a n-hexyl group, an isohexyl group, a cyclopropyl group, a cyclopentyl group, a cyclohexyl group, etc.

The carboxylalkyl group shown by $R^{25}$ and $R^{27}$ includes one derived by substituting a part of the hydrogen atoms of the lower alkyl groups mentioned above with a carboxyl group, which is specifically exemplified by a carboxymethyl group, a carboxyethyl group, a carboxypropyl group, a carboxybutyl group, a carboxypentyl group, a carboxyhexyl group, etc.

The alkyloxycarbonyl group shown by $R^{25}$ to $R^{27}$ includes preferably one having 2 to 11 carbon atoms, which is specifically exemplified by a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group, a decyloxycarbonyl group, etc.

The halogen atom shown by $R^{26}$ and $R^{27}$ includes a fluorine atom, a chlorine atom, a bromine atom and an iodine atom.

The haloalkyl group shown by $R^{27}$ includes one having 1 to 6 carbon atoms derived by halogenating (e.g. fluorinating, chlorinating, brominating, iodinating, etc.) the lower alkyl group mentioned above, which is specifically exemplified by a chloromethyl group, a bromomethyl group, a trifluoromethyl group, a 2-chloroethyl group, a 3-chloropropyl group, a 3-bromopropyl group, a 3,3,3-trifluoropropyl group, a 4-chlorobutyl group, a 5-chloropentyl group, a 6-chlorohexyl group, etc.

The aryl group in the aryl group which may have a substituent shown by $R^{27}$ includes a phenyl group, a tolyl group, a xylyl group, a naphthyl group, and the substituent includes a lower alkoxy group, and the specific examples thereof are a methoxyphenyl group, a tert-butoxyphenyl group, etc.

The aliphatic heterocyclic group shown by $R^{27}$ includes preferably 5- or 6-membered one containing 1 to 3 hetero atoms such as a nitrogen atom, an oxygen atom and a sulfur atom, and the specific examples are a pyrrolidyl-2-one group, a piperidyl group, a piperidino group, a piperazinyl group, a morpholino group, etc.

The aromatic heterocyclic group shown by $R^{27}$ includes 5- or 6-membered one containing 1 to 3 hetero atoms such as a nitrogen atom, an oxygen atom and a sulfur atom, and the specific examples are a pyridyl group, an imidazolyl group, a thizolyl group, a furanyl group and a pyranyl group.

The cyano-containing alkyl group shown by $R^{27}$ includes one derived by substituting a part of the hydrogen atoms of the lower alkyl groups mentioned above with a cyano group, which is specifically exemplified by a cyanomethyl group, a 2-cyanoethyl group, a 2-cyanopropyl group, a 3-cyanopropyl group, a 2-cyanobutyl group, a 4-cyanobutyl group, a 5-cyanopentyl group, a 6-cyanohexyl group, etc.

The acyloxy group shown by $R^{27}$ includes one having 2 to 20 carbon atoms derived from a carboxylic acid, which is specifically exemplified by an acetyloxy group, a propionyloxy group, a butylyloxy group, a pentanoyloxy group, a hexanoyloxy group, a heptanoyloxy group, an octanoyloxy group, a nonanoyloxy group, a decanoyloxy group, a benzoyloxy group, etc.

The N-alkylcarbamoyloxy group shown by $R^{27}$ includes one derived by substituting a part of the hydrogen atoms of carbamoyl group with an alkyl group, which is specifically exemplified by a n-methylcarbamoyl group, a n-ethylcarbamoyl group, a n-n-propylcarbamoyl group, a n-isopropylcarbamoyl group, a n-n-butylcarbamoyl group, a n-t-butylcarbamoyl group, etc.

The case where $R^{25}$ and $R^{26}$ are bound together with the adjacent —C=C— group to form alicyclic ring includes one where an unsaturated alicyclic ring having 5 to 10 carbon atoms is formed, and the specific examples of those groups are a norbornene ring, a cyclopentene ring, a cyclohexene ring, a cyclooctene ring, a cyclodecene ring, etc.

The specific examples of the α,β-ethylenically unsaturated monomer includes an ethylenically unsaturated aliphatic hydrocarbon having 2 to 20 carbon atoms such as ethylene, propylene, butylene and isobutylene, an ethylenically unsaturated aromatic hydrocarbons having 8 to 20 carbon atoms such as styrene, 4-methylstyrene, 4-ethylstyrene and divinylbenzene, an alkenyl ester having 3 to 20 carbon atoms such as vinyl formate, vinyl acetate, vinyl propionate and isopropenyl acetate, a halogen-containing ethylenically unsaturated compound such as vinyl chloride, vinylidene chloride, vinylidene fluoride and tetrafluoroethylene, an ethylenically unsaturated carboxylic acid (it may form an alkaline metal salt such as sodium salt and potassium salt, an ammonium salt, etc) having 3 to 20 carbon atoms such as acrylic acid, methacrylic acid, itaconic acid, maleic acid, fumaric acid, crotonic acid, vinylacetic acid, allylacetic acid and vinylbenzoic acid, an ethylenically unsaturated carboxylic acid ester such as methyl methacrylate, ethyl methacrylate, propyl methacrylate, butyl methacrylate, 2-ethylhexyl methacrylate, methyl acrylate, ethyl acrylate, butyl acrylate, 2-ethylhexyl acrylate, lauryl methacrylate, stearyl methacrylate, methyl acrylate, ethyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenoate, a cyano-containing ethylenically unsaturated compound having 3 to 20 carbon atoms such as acrylonitrile, methacrylonitrile and allyl cyanide, an ethylenically unsaturated amide compound having 3 to 20 carbon atoms such as acrylamide and methacrylamide, an ethylenically unsaturated aldehyde having 3 to 20 carbon atoms such as acrolein and croton aldehyde, an ethylenically unsaturated aliphatic heterocyclic amine having 5 to 20 carbon atoms such as N-vinylpyrrolidone and vinylpiperidine, an ethylenically unsaturated aromatic heterocyclic amine having 5 to 20 carbon atoms such as vinylpyridine and 1-vinylimidazole, etc.

Those monomers may be used alone or in a suitable combination of two or more thereof.

The above polymerization includes a solution polymerization, a bulk polymerization, a suspension polymerization, an emulsion polymerization, etc.

The polymerization solvent includes a halogenated hydrocarbon such as chloroform, methylene chloride and 1,2- dichloroethane, a hydrocarbon such as toluene, benzene and xylene, N,N-dimethylformamide, dimethylsulfoxide, etc. Those solvents may be used alone or in a suitable combination of two or more thereof.

The polymerization is desirably conducted under an inert gas atmosphere. The inert gas includes nitrogen gas, argon gas, etc.

An amount of the sulfonium salt compound of the present invention varies depending on the kind of a, 1-ethylenically unsaturated monomer and generally 0.1 to 200 wt %, preferably 1 to 50 wt % relative to the α,β-ethylenically unsaturated monomer.

A concentration of the α,β-ethylenically unsaturated monomer upon polymerization is varied with the kind of the α, β-ethylenically unsaturated monomer and generally 1 to 100 wt % (no solvent), preferably 10 to 80 wt %.

A polymerization temperature is generally −78 to 100° C., preferably −20 to 50° C.

A polymerization time varies depending upon the polymerization temperature, the kinds of the sulfonium salt of the present invention and the α, β-ethylenically unsaturated monomer, their concentration and other reaction conditions and is generally 1 to 50 hours.

Treatments and the like after the reaction can be conducted after conventional manner that has so far been conducted in this field of technology.

The sulfonium salt compound of the present invention is easily warped because it contains a substituent at the o- and/or m-position of the aromatic ring and can easily be decomposed by exposing to UV, deep UV, excimer laser or irradiation with electron beams, X-rays, etc. to generate an acid, and therefore when the compound is used as an acid generator for chemically amplified resists, ultra-fine pattern profile can obtained and roughness of side walls can be improved.

Further, the sulfonium salt compound of the present invention can generate an acid by irradiation with light and therefore the compound is useful also as a cationic photo polymerization initiator.

In the following, the present invention is explained in detail referring to examples, but the present invention is not limited thereto by any means.

EXAMPLE

Example 1

Synthesis of Diphenyl-o-methylphenylsulfonium p-Toluenesulfonate (Method A)

In 370 ml of methylene chloride was dissolved 21.1 g (0.1 mole) of diphenylsulfoxide and 27.8 g (0.13 mole) of trimethylsilyltrifluoromethane sulfonate was added dropwise thereto at −70 to −60° C. under nitrogen stream, followed by stirring at 0 to 5° C. for 30 minutes. Then Grignard reagent prepared from 50 g (0.29 mole) of o-bromotoluene and 5.1 g of magnesium turning in tetrahydrofuran after a conventional manner was added dropwise to the resultant at −70 to −60° C., followed by allowing a reaction to take place at 0 to 50° C. with stirring for 30 minutes. After the reaction, 10% of aqueous ammonium chloride solution was poured into the resultant and an organic layer obtained by separation was washed with water three times and dried over anhydrous $MgSO_4$. The drying agent was removed by filtration and the solvent was removed and the resulting oily substance was crystallized from butyl acetate, followed by recovering by filtration and drying, whereby 19.3 (Yield: 43%) g of diphenyl-o-methylphenylsulfonium trifluoromethanesulfonate was obtained as white crystal.

Melting point: 131–132.4° C.; $^1$HNMR (CDCl$_3$) δ ppm: 2.58 (3H, s, CH$_3$), 7.09 (1H, s, CH$_3$), 7.49–7.53 (2H, m, Ar—H), 7.64–7.81 (11H, m, Ar—H).

In aqueous methanol solution was dissolved 18.8 g (44 mmole) of the resulting diphenyl-o-methylphenylsulfonium trifluoromethanesulfonate and passed through an activated strong base type anion exchange resin (Amberlite IRA-900; mfd. by Organo Corporation.). To the eluting solution was added 10.0 g (53 mmole) of p-toluenesulfonic acid monohydrate, followed by allowing a reaction to take place at room temperature for 1 hour with stirring. After the reaction, the solvent was removed and the residue was dissolved in 200 ml of methylene chloride, washed with water three times and concentrated under reduced pressure to give 17.2 g (Yield: 91%) of diphenyl-o-methylphenylsulfonium p-toluenesulfonate as white crystal.

The compound was confirmed as totally ortho-type compound by HPLC measurement.

Melting point: 144.9–146.40° C.; $^1$HNMR (CDCl$_3$) δ ppm: 2.30, 2.58 (each 3H, s, CH$_3$), 7.03–7.07(3H, dd, Ar—H), 7.40–7.46 (2H, m, Ar—H), 7.58–7.81 (13H, m, Ar—H).

Example 2

Synthesis of Diphenyl-m-methylphenylsulfonium p-Toluenesulfonate (Method B)

In 600 ml of tetrahydrofuran was dissolved 24.02 g of diphenyl sulfoxide under nitrogen stream, and 31.5 g of chlorotrimethylsilane was poured thereinto. A Grignard reagent prepared from 50 g of m-bromotoluene and 4.70 g of magnesium turning after a conventional manner was added dropwise thereto under ice-cooling, followed by allowing a reaction to take place at the same temperature for 3 hours. After the reaction, 480 ml of 24% aqueous hydrobromic acid solution was added dropwise to the reaction solution at 0 to 5° C., and then 600 ml of toluene was poured thereinto, followed by stirring and separation, and the resulting organic layer was extracted twice each with 120 ml of 12% aqueous hydrobromic acid solution, and the resulting aqueous layers were combined and further extracted three times each with 480 ml of methylene chloride. The resulting organic layer was dried over anhydrous $MgSO_4$ and concentrated under reduced pressure to give 19.66 g (Yield: 46%) of diphenyl-mmethylphenylsulfonium bromide as white crystal.

Melting point: 173.9–174.5° C. $^1$HNMR (CDCl$_3$) δ ppm: 2.46 (6H, s, CH$_3$), 7.58–7.87 (14H, m, Ar—H).

In 50 ml of methylene chloride was dissolved 12.51 g of the resulting diphenyl-m-methylphenylsulfonium bromide at the room temperature under a shade and 9.77 g of silver p-toluenesulfonate was added thereto, followed by allowing a reaction to take place at room temperature overnight with stirring. After the reaction, the resulting precipitate was removed by filtration and the mother liquor was concentrated under reduced pressure to give 11.34 g (Yield: 72%) of diphenyl-m-methylphenylsulfonium p-toluenesulfonate as white crystal.

Melting point: 126.7–128.7° C. $^1$HNMR (CDCl$_3$) δ ppm: 2.31 (3H, s, CH$_3$), 2.41 (3H, s, CH$_3$), 7.08 (2H, d, J=Ar—H), 7.50–7.51 (3H, s, Ar—H), 7.63–7.82 (13H, m, Ar—H).

Example 3

Synthesis of Diphenyl-2,4,6-trimethylphenylsulfonium p-Toluenesulfonate (Method A)

In 36.1 g (0.3 mole) of mesitylene was dissolved 6.1 g (0.03 mole) of diphenylsulfoxide, and 12.6 g (0.06 mole) of trifluoroacetic anhydride was poured thereinto under cooling at 5° C. or lower and further 4.5 g (0.03 mole) of trifluoromethane sulfonic acid was added dropwise thereto at −5 to 5° C., followed by allowing a reaction to take place at the same temperature for 2 hours with stirring. Into the resultant was poured 20 ml of n-hexane, followed by separation. This process step series was conducted three times and the resulting crude oily substance was crystallized from a mixture of butyl acetate and isopropyl ether and the crystal was recovered by filtration and dried to give 11.5 g (Yield: 84%) of diphenyl-2,4,6-trimethylphenylsulfonium trifluoromethanesulfonate as white crystal.

Melting point: 113.0–113.5° C.; $^1$HNMR (CDCl$_3$) δ ppm: 2.31 (6 H, s, CH$_3$), 2.42 (3H, s, CH$_3$), 7.20 (2H, s, Ar—H) 7.59–7.62 (4H, m, Ar—H), 7.71–7.77 (6H, m, Ar—H).

10.0 g of the resulting diphenyl-2,4,6-trimethylphenylsulfonium trifluoromethanesulfonate was treated in the same manner as in Example 1 to give 10.5 g (Yield: 100%) of diphenyl-2,4,6-trimethylphenylsulfonium p-toluenesulfonate as white crystal.

Melting point: 112.5–113° C.; $^1$HNMR (CDCl$_3$) δ ppm: 2.29 (3H, s, CH$_3$), 2.31 (6H, s, CH$_3$), 2,39 (3H, s, CH$_3$), 7.03 (2H, d, J=8.1 Hz, Ar—H), 7.15 (2H, s, Ar—H), 7.64–7.73 (12H, m, Ar—H).

Example 4 to 11

With the use of diphenylsulfoxide and the desired benzene derivatives, synthesis was conducted after any one of methods described in Example 1 to 3 to give the corresponding diphenyl-alkyl substituted phenylsulfonium aromatic sulfonate. The result obtained is shown in Table 1 to 3.

TABLE 1

| Exp. | Benzene Derivative | Method | Product | Physical property | $^1$HNMR (CDCl$_3$) δ ppm |
|---|---|---|---|---|---|
| 4 | m-xylene | Exp. 2 | Diphenyl-2,4-dimethylphenyl sulfonium p-toluenesulfonate | White crystal mp. 43.5–49.3° C. | 2.29, 2.40, 2.53 (each 3H, s, CH$_3$), 6.93, 7.21 (each 1H, d, J=8.2Hz, aromatic ring H), 7.04(2H, d, J=7.8Hz, aromatic ring H), 7.25 (1H, s, aromatic ring H), 7.64–7.78(12H, m, aromatic ring H) |
| 5 | o-bromo toluene | Exp. 3 | Diphenyl-o-methylphenyl sulfonium p-toluenesulfonate | White crystal mp. 145.5–146.5° C. | Same as Exp. 1 |
| 6 | o-bromo toluene | Exp. 1 | Diphenyl-o-methylphenylsulfonium benzenesulfonate | Pale yellowish viscous oil | 2.59(3H, s, CH$_3$), 7.05 (1H, d, J=8.3 Hz, aromatic ring H), 7.25–7.28(4H, m, aromatic ring H), 7.43–7.48(2H, m, aromatic ring H), 7.60–7.90(aromatic ring H) |

TABLE 2

| Exp. | Benzene Derivative | Method | Product | Physical Property | $^1$HNMR (CDCl$_3$) δ ppm |
|---|---|---|---|---|---|
| 7 | o-bromo ethyl benzene | Exp. 1 | Diphenyl-o-ethylphenyl sulfonium p-toluenesulfonate | Pale yellowish viscous oil | 1.14(3H, t, J=7.3Hz, CH$_3$), 2.29(3H, s, CH$_3$), 2.98(2H, q, J=7.3Hz, CH$_2$), 7.04 (2H, d, J=8.1Hz, aromatic ring H), 7.13(1H, d, J=8.3Hz, aromatic ring H), 7.74–7.53(2H, m, aromatic ring H), 7.65–7.78(13H, m, aromatic ring H) |
| 8 | o-bromo toluene | Exp. 1 | Diphenyl-o-methylphenyl sulfonium 1-naphthalene sulfonate | Pale yellowish crystal m.p.188.2–188.7° C. | 2.43(3H, s, CH$_3$), 6.94(1H, d, J=8.4, aromatic ring H), 7.25–7.75(18H, m, aromatic ring H), 8.17(1H, d, J=7.2Hz, aromatic ring H), 9.08(1H, d, J=5.5Hz, aromatic ring H) |

TABLE 2-continued

| Exp. | Benzene Derivative | Method | Product | Physical Property | $^1$HNMR (CDCl$_3$) δ ppm |
|---|---|---|---|---|---|
| 9 | mesitylene | Exp. 1 | Diphenyl-2,4,6-trimethylphenyl sulfonium 1-naphthalene sulfonate | Pale brownish crystal m.p.187–192° C. | 2.28(6H, s, CH$_3$), 2.37(3H, s, CH$_3$), 7.10 (1H, d, naphthalene ring H), 7.38–7.40 (2H, m, naphthalene ring H), 7.61–7.66 (10H, m, aromatic ring H), 7.72–7.75 (2H, m, naphthalene ring H), 8.10(1H, d, naphthalene ring H), 9.00(1H, d, naphthalene ring H) |
| 10 | o-bromo toluene | Exp. 1 | Diphenyl-o-methylphenyl sulfonium 4-ethylbenzene sulfonate | White crystal m.p. 145.2–146.2° C. | 1.17(3H, t, J=7.6Hz, CH$_3$), 2.55(3H, s, CH$_3$), 2.59(2H, q, J=7.6 Hz, CH$_2$), 7.03–7.20(3H, m, aromatic ring H), 7.40–7.46(2H, m, aromatic ring H), 7.58–7.80(13H, m, aromatic ring H) |

TABLE 3

| Exp. | Benzene Derivative | Method | Product | Physical Property | $^1$HNMR (CDCl$_3$), δ ppm |
|---|---|---|---|---|---|
| 11 | o-bromo toluene | Exp. 1 | Diphenyl-o-methyl-phenyl sulfonium dodecyl-benzene sulfonate | Pale yellowish viscous oil | 0.80–0.89(5H, m, CH$_3$), 1.07–1.23(16H, m, CH$_2$), 143–158 (2H, m, CH$_2$), 2.42–2.45(2H, m, CH$_2$), 2.57(3H, s, CH$_3$), 7.01–7.05(3H, m, aromatic ring, H), 7.39–7.45(2H, m, aromatic ring, H), 7.56–7.81(13H, m, aromatic ring H) |

Example 12

Synthesis of Diphenyl-2,4,6-trimethylphenylsulfonium 1-Octanesulfonate (Method C)

To 38 g of diphenyl sulfoxide were added 500 ml of mesitylene and 340 g of aluminum bromide, followed by allowing a reaction to take place at 90° C. for 12 hours. After the reaction solution was cooled, a mixture of 100 ml of concentrated hydrobromic acid solution and 500 ml of ice water were poured. An aqueous layer was extracted with benzene and the organic layer was washed with water and dried over anhydrous MgSO$_4$, followed by filtration and removal of the solvent, whereby 58 g (Yield: 80%) of diphenyl-2,4,6-trimethylphenylsulfonium bromide was obtained as white crystal.

In 40 ml of methylene chloride was dissolved 4.2 g of the obtained diphenyl-2,4,6-trimethylphenylsulfonium bromide and cooled to 5° C., and then 8.1 g of silver 1-octane-sulfonate was added, followed by allowing a reaction to take place with stirring for 8 hours; The precipitated silver bromide was filtered and washed with water, followed by drying over anhydrous MgSO$_4$, filtration and removal of the solvent, whereby 7.9 g (Yield: 95%) of diphenyl-2,4,6-trimethylphenylsulfonium 1-octanesulfonate was obtained as white crystal.

Melting point: 110–112° C.; $^1$HNMR (CDCl$_3$) δ ppm: 0.85 (t, 3H), 1.20–1.24 (m, 10H), 1.75–1.85 (m, 2H), 2.35 (s, 6H), 2.41 (s, 3H), 2.72–2.76 (m, 2H), 7.17 (s, 2H), 7.70–7.80 (m, 10H), IR (KBr) cm$^{-1}$: 3063, 2930, 2855, 1478, 1456, 1196, 1036, 758.

Example 13

Synthesis of Diphenyl-2,4,6-trimethylphenylsulfonium 1-Perfluorooctanoate

In 40 ml of methylene chloride was dissolved 4 g of diphenyl-2,4,6-trimethylphenylsulfonium bromide obtained in Example 12 and cooled to 5° C., and then 8.1 g of silver 1-perfluorooctanesulfonate was added thereto. Precipitated silver bromide was filtered and washed with water, followed by drying over anhydrous MgSO$_4$, filtration and removal of the solvent, whereby 7.9 g (Yield: 95%) of diphenyl-2,4,6-trimethylphenylsulfonium 1-perfluorooctanesulfonate was obtained as white crystal.

Melting point: 112–114° C.; $^1$HNMR (CDCl$_3$) δ ppm: 2.32 (s, 6H), 2.41 (s, 3H), 7.18 (s, 2H), 7.68–7.73 (m, 10H IR (KBr) cm$^{-1}$: 3063, 1449, 1354, 1233, 1009, 509.

Example 14

Synthesis of Diphenyl-2,4,6-trimethylphenylsulfonium p-Trifluoromethyl Benzoate In 40 ml of methylene chloride was dissolved 4.2 g of diphenyl-2,4,6-trimethylphenylsulfonium bromide obtained in Example 12 and cooled to 5° C., and then 3.7 g of silver 4-trifluoromethyl benzoate was added thereto, followed by allowing a reaction to take place with stirring for 8 hours. Precipitated silver bromide was filtered and washed with water, whereby 3.6 g (Yield: 71%) of diphenyl-2,4,6-trimethylphenylsulfonium p-trifluoromethyl benzoate was obtained as white crystal.

Melting point: 132–134° C.; $^1$HNMR (CDCl$_3$) δ ppm: 2.30 (s, 6H), 2.38 (s, 3H), 7.14 (s, 2H), 7.45 (d, 2H), 7.68–7.75 (m, 10H), 8.10 (d, 2H) IR (KBr) cm$^{-1}$: 3441, 1734, 1445, 1327, 1157, 1067, 1017, 760.

Comparative Example 1

Synthesis of Diphenyl-p-methylphenylsulfonium p-Toluene Sulfonate

The same reaction and after treatment as Example 1 were conducted except for using p-bromotoluene in place of o-bromotoluene to give diphenyl-p-methylphenyl sulfonium p-toluenesulfonate.

The obtained compound was confirmed as totally para-compound by HPLC measurement.

Comparative Example 2

Synthesis of Diphenyl-p-methylphenylsulfonium p-Toluenesulfonate

The same reaction and after treatment as Example 3 were conducted except for using toluene in place of mesitylene to give diphenyl-p-methylphenylsulfonium p-toluenesulfonate.

The obtained compound was confirmed as one containing 5% of o-isomer by HPLC measurement.

Comparative Example 3

Synthesis of Diphenyl-m-tert-butoxyphenylsulfonium p-Toluenesulfonate (1) In 250 ml of methylene chloride was dissolved 25.1 g (0.145 mole) of m-bromophenol and 3.2 g of trifluoromethane sulfonic acid was added thereto under nitrogen stream at −45° C. or lower and further 53 g of an isobutene was introduced thereto at −55 to −50° C., followed by allowing a reaction to take place with stirring at the same temperature for 3 hours. After the reaction, 2.7 g of triethylamine was added dropwise to the reaction solution and temperature was increased up to room temperature, and the resultant was washed with water and the organic layer is concentrated to give 66.7 g of a residue, which was then distilled under a reduced pressure to give 31.7 g of m-tert-butoxybromobenzene as a colorless oily substance (b.p. 76 to 80° C./0.27 kPa).

$^1$HNMR δ ppm (CDCl$_3$): 1.34 (9H, s, CH$_3$), 7.11 (1H, m, Ar—H), 7.16 (3H, m, Ar—H).

(2) In 100 ml of methylene chloride was dissolved 14.2 g (70 mmole) of diphenylsulfoxide and 5.1 g of triethylamine was poured thereinto and further 14.6 g of trimethylsilyl chloride was added dropwise thereto at −5 to 0° C., followed by stirring at 0±2° C. for 20 sec., and a Grignard reagent prepared from 30.9 g (0.135 mole) of m-tert-butoxybromobenzene obtained in the above (1) and 3.3 g of a magnesium turning was added dropwise to the resultant at 0 to 10° C., followed by allowing a reaction to take place at the same temperature with stirring for 1 hour, and the reaction solution was poured into an aqueous ammonium chloride solution, followed by conducting a conventional treatment to give 18.7 g of diphenyl-m-tert-butoxyphenylsulfonium chloride as an orange yellow viscous oily substance.

$^1$HNMR δ ppm (CDCl$_3$): 1.34 (9H, s, CH$_3$), 7.31–7.34 (1H, m, Ar—H), 7.53 (1H, m, Ar—H), 7.59–7.63 (1H, m, Ar—H), 7.69–7.77 (7H, m, Ar—H), 7.87–7.89 (4H, m, Ar—H).

(3) In 20 ml of methylene chloride was dissolved 5.6 g (15 mmole) of diphenyl-m-tert-butoxyphenylsulfonium chloride obtained in the above (2) and 4.6 g (16.5 mmole) of silver p-toluenesulfonate was added thereto, followed by allowing a reaction to take place at room temperature with stirring for 2 hours. After the reaction, the resultant was subjected to a filtration and the filtrate was washed with water and the organic layer was concentrated. The residue was crystallized from n-hexane and filtered and dried to give 5.7 g of diphenyl-m-tert-butoxyphenylsulfonium p-toluenesulfonate as a white waxy crystal.

$^1$HNMR δ ppm (CDCl$_3$): 1.31 (9H, s, CH$_3$), 2.31 (9H, s, CH$_3$), 7.07–7.09 (2H, m, Ar—H), 7.27 (1H, m, Ar—H), 7.51–7.53 (2H, m, Ar—H), 7.62–7.66 (5H, m, Ar—H), 7.69–7.71 (2H, m, Ar—H), 7.79–7.81 (6H, m, Ar—H).

Comparative Example 4

Synthesis of Diphenyl-2,4,6-trimethylphenylsulfonium 2,4,6-Trimethoxybenzenesulfonate (1) According to a method described in [C. M. Paleos et al., J. Org. Chem. 39(24), 3594, (1974)], 16.8 g (0.1 mole) of 1,3,5-trimethoxybenzene was reacted with 35.0 g of chlorosulfonic acid in 250 ml of chloroform at −5 to 0° C., and after the reaction, the reaction solution was treated after a conventional manner, and 15.2 g of the residue was crystallized from n-hexane, filtered and dried to give 12.6 g of 2,4,6-trimethoxybenzenesulfonyl chloride as a pinkish prism crystal.

$^1$HNMR δ ppm (CDCl$_3$): 3.77 (9H, s, CH$_3$O), 6.09 (2H, s, Ar—H).

(2) To 54.7 g of 15% aqueous tetramethylammonium hydroxide solution was gradually added 12.0 g (0.045 mole) of 2,4,6-trimethoxybenzenesulfonyl chloride obtained in the above (1) at 75 to 80° C., followed by allowing a reaction to take place at 80° C. with stirring for 3 hours. After the reaction, the reaction solution was treated after a conventional manner, and 19.9 g of the residue was crystallized from acetone and filtered and dried to give 13.0 g of 2,4,6-trimethoxybenzenesulfonic acid tetramethylammonium as a hygroscopic pale yellow crystal.

(3) In a mixture of 60 ml of water and 20 ml of methylene chloride, 6.1 g (18 mmole) of diphenyl-2,4,6-trimethylphenylsulfonium chloride obtained by the same procedure and after treatment as Example 2 except using mesityl chloride in place of m-bromotoluene was reacted with 7.4 g (23 mmole) of tetramethylammonium 2,4,6-trimethoxybenzenesulfonate obtained in the above (2) at room temperature with stirring for 3 hours. After the reaction, the reaction solution was treated after a conventional manner to give 2.3 g of diphenyl-2,4,6-trimethylphenyl sulfonium 2,4,6-trimethoxybenzenesulfonate as a colorless syrupy crystal.

$^1$HNMR δ ppm (CDCl$_3$): 2.34 (6H, s, CH$_3$O), 2.39 (3H, s, CH$_3$O), 3.79 (3H, s, CH$_3$), 3.85 (6H, s, CH$_3$), 6.07 (2H, s, Ar—H), 7.13 (2H, s, Ar—H), 7.68–7.69 (6H, m, Ar—H), 7.74–7.77 (4H, m, Ar—H).

Experimental Example 1

A mixed solution comprising the following ingredients was filtered with a filter of 0.1 μm mesh to prepare a chemically amplified resist composition.
(1) Poly(p-1-ethoxyethoxystyrene/p-tert-butoxycarbonyloxystyrene/p-hydroxystyrene)
   [Mw 20000; Mw/Mn 1.12] 6.0 g
(2) bis(cyclohexylsulfonyl)diazomethane 0.2 g
(3) diphenyl-o-methylphenyl sulfonium p-toluenesulfonate
   [compound of Example 1] 0.1 g
(4) tri-n-butylamine 0.1 g
(5) fluorine-containing nonionic surfactant [commercially available product] 0.1 g
(6) propyleneglycol monomethyl ether acetate 28.5 g The above resist composition was stored at 23° C. and the number of fine particles in the composition were measured at predetermined timing so as to evaluate its storage stability. The measurement of the particles was conducted by using a particle counter (KL20A; mfd. by Rion Corporation Limited.). The result is shown in Table 4.

Further, a pattern was formed with the use of the above resist composition after the following process.

An anti-reflective coating (DUV-32; mfd. by Brewer Science. Inc.) was spin-coated on a silicone wafer, followed by a heat treatment at 200° C. for 60 sec. on a hot plate to form an anti-reflective film of 0.52 μm thick. And then, the above resist composition was spin-coated on the film, followed by pre-baking at 100° C. for 90 sec. on a hot plate to give a resist film of 0.7 μm thick. Then a selective exposure was conducted on the resist film through a mask with the use of a KrF excimer laser stepper (NA 0.55), followed by post exposure baking (abbreviated as PEB) at 110° C. for 90 sec. on a hot plate and developing with the use of an alkaline developing solution (2.38% aqueous tetramethylammonium hydroxide solution) for 60 sec. so as to dissolve and remove only the exposure portion, whereby a positive tone pattern was obtained. The resulting positive tone pattern was of a rectangular shape and showed a definition of 0.15 μm Line and Space (abbreviated as L&S) under an exposure dose of 28 mj/cm$^2$. In case of a defocus exposure, DOF was ±0.5 μm under 0.20 μm L&S.

With the use of the above resist composition, a change of pattern size in relation to Post Exposure Delay during the period from the exposure to the PEB was measured, whereby no change of pattern size under 0.18 μm L&S was observed even after 2 hours, and thus high storage stability was confirmed.

The above resist composition was spin-coated on a silicone wafer, followed by pre-baking at 90° C. for 90 sec. on a hot plate to give a resist film of 1.0 μm thick. Then a selective exposure through a mask was conducted with the use of a KrF excimer laser stepper, followed by PEB at 90° C. for 60 sec. on a hot plate and developing with the use of an alkaline developing solution for 60 sec. to give a positive tone pattern. On thus obtained pattern, a sensitivity (Eth) was measured, and exposure dose resolving 0.25 ft m L&S at 1:1 was defined as the most suitable exposure dose (Eop), and the minimum line and space resolved by the Eop was defined as the resolution of a resist. Consequently, 0.18 μm L&S dissolution under an exposure dose of 42 mJ/cm$^2$ was attained, and the shape was such a good one as rectangular. A pattern edge roughness of 0.22 μm L&S was also measured by a scanning electric microscope, whereby the roughness was found to be such a mall as 12 nm.

TABLE 4

| Storage day | 0 day | 3 days | 1 week | 2 weeks | 1 month | 2 months | 3 months | 6 months |
| --- | --- | --- | --- | --- | --- | --- | --- | --- |
| Number of fine particles | ≦10 | ≦10 | ≦10 | 15 | 14 | 15 | 20 | 25 |

*unit: number/ml.
Particle size: ≧0.2 μm

Experimental Examples 2 to 10

Resist solutions were prepared by using the sulfonium salts (in the same amount) in the following Table 5 in place of diphenyl-o-methylphenylsulfonium p-toluenesulfonate in the components in Experimental Example 1 and then a measurement of fine particles was conducted by the same manner as described in Experimental Example 1. The result is shown in Table 6

TABLE 5

| | |
| --- | --- |
| Experimental Example 2 | diphenyl-m-methylphenyl sulfonium p-toluene sulfonate [compound of Example 2] |
| Experimental Example 3 | diphenyl-2,4,6-trimethylphenyl sulfonium p-toluene sulfonate [compound of Example 3] |

TABLE 5-continued

| | |
|---|---|
| Experimental Example 4 | diphenyl-2,4-dimethylphenyl sulfonium p-toluene sulfonate [compound of Example 4] |
| Experimental Example 5 | diphenyl-o-methylphenyl sulfonium benzene sulfonate [compound of Example 6] |
| Experimental Example 6 | diphenyl-o-ethylphenyl sulfonium p-toluene sulfonate [compound of Example 7] |
| Experimental Example 7 | diphenyl-o-methylphenyl sulfonium 1-naphthalene sulfonate [compound of Example 8] |
| Experimental Example 8 | diphenyl-2,4,6-trimethylphenyl sulfonium 1-naphthalene sulfonate [compound of Example 9] |
| Experimental Example 9 | diphenyl-o-methylphenyl sulfonium 4-ethylbenzene sulfonate [compound of Example 10] |
| Experimental Example 10 | Diphenyl-o-methylphenyl sulfonium dodecylbenzene sulfonate [compound of Example 11] |

TABLE 6

| Storage day | 0 day | 3 days | 1 week | 2 weeks | 1 month | 2 months | 3 months | 6 months |
|---|---|---|---|---|---|---|---|---|
| Expt.2 | ≦10 | ≦10 | ≦10 | 15 | 20 | 20 | 25 | 25 |
| Expt.3 | ≦10 | ≦10 | ≦10 | 15 | 15 | 15 | 20 | 20 |
| Expt.4 | ≦10 | ≦10 | ≦10 | 15 | 15 | 15 | 20 | 20 |
| Expt.5 | ≦10 | ≦10 | ≦10 | 15 | 20 | 25 | 30 | 40 |
| Expt.6 | ≦10 | ≦10 | ≦10 | 15 | 20 | 25 | 30 | 30 |
| Expt.7 | <10 | ≦10 | ≦10 | 15 | 20 | 30 | 40 | 55 |
| Expt.8 | <10 | ≦10 | ≦10 | 15 | 20 | 30 | 45 | 55 |
| Expt.9 | ≦10 | ≦10 | ≦10 | 15 | 20 | 25 | 30 | 30 |
| Expt.10 | <10 | ≦10 | ≦10 | 15 | 20 | 25 | 35 | 50 |

*unit: number/ml.
Particle size: ≧0.2 μm

Further, patterns were formed with the use of the resist solutions after the same manner as described in Experimental Example 1. The result on an anti-reflective film is shown in Table 7 and the result on a silicone wafer is shown in Table 8.

TABLE 7

| | Dose mJ/cm$^2$ | Dissolution μm L&S | Shape | DOF 0.20 μm L&S | Delay time 0 minute | After 2 hours |
|---|---|---|---|---|---|---|
| Expt. Exp.2 | 30 | 0.15 | Rectangular | +0.5 μm | 0.18 μm L&S | 0.18 μm L&S |
| Expt. Exp.3 | 28 | 0.15 | Rectangular | +0.5 μm | 0.18 μm L&S | 0.18 μm L&S |
| Expt. Exp.4 | 32 | 0.15 | Rectangular | +0.5 μm | 0.18 μm L&S | 0.18 μm L&S |
| Expt. Exp.5 | 28 | 0.15 | Rectangular | +0.5 μm | 0.18 μm L&S | 0.18 μm L&S |
| Expt. Exp.6 | 30 | 0.15 | Rectangular | +0.5 μm | 0.18 μm L&S | 0.18 μm L&S |
| Expt. Exp.7 | 35 | 0.16 | Rectangular | +0.4 μm | 0.18 μm L&S | 0.18 μm L&S |
| Expt. Exp.8 | 35 | 0.16 | Rectangular | +0.4 μm | 0.18 μm L&S | 0.18 μm L&S |
| Expt. Exp.9 | 30 | 0.15 | Rectangular | +0.5 μm | 0.18 μm L&S | 0.18 μm L&S |
| Expt. Exp.10 | 30 | 0.15 | Rectangular | +0.5 μm | 0.18 μm L&S | 0.18 μm L&S |

TABLE 8

| | Dose mJ/cm$^2$ | Dissolution Mm L&S | Shape | Edge roughness 0.22 μm L&S |
|---|---|---|---|---|
| Expt. Exp.2 | 45 | 0.18 | Rectangular | 15 nm |
| Expt. Exp.3 | 42 | 0.18 | Rectangular | 10 nm |
| Expt. Exp.4 | 48 | 0.18 | Rectangular | 14 nm |
| Expt. Exp.5 | 42 | 0.18 | Rectangular | 15 nm |
| Expt. Exp.6 | 44 | 0.18 | Rectangular | 15 nm |
| Expt. Exp.7 | 52 | 0.20 | Rectangular | 20 nm |
| Expt. Exp.8 | 52 | 0.20 | Rectangular | 20 nm |
| Expt. Exp.9 | 44 | 0.18 | Rectangular | 12 nm |
| Expt. Exp.10 | 45 | 0.18 | Rectangular | 18 nm |

Experimental Examples 11 to 16

The mixed solutions comprising the components in the following Table 9 were filtered with use of a filter to prepare chemically amplified resist compositions.

TABLE 9

| | | |
|---|---|---|
| Example 11 | Poly(p-1-ethoxyethoxystyrene/p-pivaloyloxyoxystyrene/p-hydroxystyrene) [Mw 20000; Mw/Mn 1.15] | 6.0 g |
| | bis (cyclohexylsulfonyl) diazomethane | 0.2 g |
| | diphenyl-2,4,6-trimethylphenyl p-toluene sulfonate [compound of Example 3] | 0.1 g |
| | dicyclohexylmethylamine | 0.1 g |
| | fluorine-containing nonionic surfactant [commercially available product] | 0.1 g |
| | propyleneglycol monomethyl ether acetate | 29.0 g |
| Example 12 | Poly(p-1-ethoxyethoxystyrene/p-pivaloyloxyoxystyrene/p-hydroxystyrene) [Mw 20000; Mw/Mn 1.15] | 6.0 g |
| | bis (cycloexylsulfonyl) diazomethane | 0.2 g |
| | diphenyl-o-methylphenyl sulfonium p-toluene sulfonate [compound of Example 1] | 0.1 g |
| | dicyclohexylmethylamine | 0.1 g |
| | fluorine-containing nonionic surfactant [commercially available product] | 0.1 g |
| | propyleneglycol monomethyl ether acetate | 29.0 g |
| Example 13 | Poly(p-1-ethoxyethoxystyrene/p-pivaloyloxyoxystyrene/p-hydroxystyrene) [Mw 20000; Mw/Mn 1.15] | 6.0 g |
| | bis (cyclohexylsulfonyl) diazomethane | 0.2 g |
| | diphenyl-m-methylphenyl sulfonium p-toluene sulfonate [compound of Example 2] | 0.1 g |
| | dicyclohexylmethylamine | 0.1 g |
| | fluorine-containing nonionic surfactant [commercially available product] | 0.1 g |
| | propyleneglycol monomethyl ether acetate | 29.0 g |
| Example 14 | Poly(p-1-ethoxyethoxystyrene/p-pivaloyloxyoxystyrene/p-hydroxystyrene) [Mw 20000; Mw/Mn 1.15] | 6.0 g |
| | bis (cyclohexylsulfonyl) diazomethane | 0.2 g |
| | diphenyl-2,4,6-trimethylphenyl sulfonium 1-octane sulfonate [compound in Example 12] | 0.1 g |
| | dicyclohexylmethylamine | 0.1 g |
| | fluorine-containing nonionic surfactant [commercially available product] | 0.1 g |
| | propyleneglycol monomethyl ether acetate | 29.0 g |
| Example 15 | Poly(p-1-ethoxyethoxystyrene/p-pivaloyloxyoxystyrene/p-hydroxystyrene) [Mw 20000; Mw/Mn 1.15] | 6.0 g |
| | bis (cyclohexylsulfonyl) diazomethane | 0.2 g |
| | diphenyl-2,4,6-trimethylphenyl sulfonium 1-perfluorooctanoate [compound in Example 13] | 0.1 g |
| | dicyclohexylmethylamine | 0.1 g |
| | fluorine-containing nonionic surfactant [commercially available product] | 0.1 g |
| | propyleneglycol monomethyl ether acetate | 29.0 g |
| Example 16 | Poly(p-1-ethoxyethoxystyrene/p-pivaloyloxyoxystyrene/p-hydroxystyrene) [Mw 20000; Mw/Mn 1.15] | 6.0 g |
| | bis (cyclohexylsulfonyl) diazomethane | 0.2 g |
| | diphenyl-2,4,6-trimethylphenyl sulfonium p-trifluoromethyl benzoate [compound in Example 14] | 0.1 g |
| | dicyclohexylmethylamine | 0.1 g |
| | fluorine-containing nonionic surfactant [commercially available product] | 0.1 g |
| | propyleneglycol monomethyl ether acetate | 29.0 g |

On the above resist composition solutions, measurement of the number of fine particles was conducted at predetermined timing under storage at 23° C. after the same manner as described in Experimental Example 1. The result is shown in Table 10

TABLE 10

| Storage day | 0 day | 3 days | 1 week | 2 weeks | 1 month | 2 month | 3 month | 6 month |
|---|---|---|---|---|---|---|---|---|
| Exper. Exp.11 | ≦10 | ≦10 | ≦10 | 15 | 15 | 15 | 20 | 20 |
| Exper. Exp.12 | ≦10 | ≦10 | ≦10 | 15 | 15 | 15 | 20 | 25 |
| Exper. Exp.13 | ≦10 | ≦10 | ≦10 | 15 | 15 | 15 | 25 | 25 |
| Exper. Exp.14 | ≦10 | ≦10 | ≦10 | ≦10 | 15 | 15 | 15 | 15 |
| Exper. Exp.15 | ≦10 | ≦10 | ≦10 | ≦10 | 15 | 15 | 15 | 20 |
| Exper. Exp.16 | ≦10 | ≦10 | ≦10 | ≦10 | 15 | 15 | 15 | 20 |

*unit: number/ml
particle size: ≧0.2 μm

Further, patterns were formed with the use of the above resist composition solutions after the same manner as described in Experimental Example 1. The result on an anti-reflective film is shown in Table 11 and the result on a silicone wafer is shown in Table 12.

TABLE 11

| | Dose mJ/cm$^2$ | Dissolution μm L&S | Shape | DOF 0.20 μm L&S | Delay time 0 minute | Delay time After 2 hr. |
|---|---|---|---|---|---|---|
| Exper. Exp.11 | 28 | 0.16 | Rectangular | ±0.4 μm | 0.18 μm L&S | 0.18 μm L&S |
| Exper. Exp.12 | 30 | 0.16 | Rectangular | ±0.4 μm | 0.18 μm L&S | 0.18 μm L&S |
| Exper. Exp.13 | 31 | 0.16 | Rectangular | ±0.4 μm | 0.18 μm L&S | 0.18 μm L&S |
| Exper. Exp.14 | 38 | 0.16 | Rectangular | ±0.4 μm | 0.18 μm L&S | 0.18 μm L&S |
| Exper. Exp.15 | 40 | 0.16 | Rectangular | ±0.4 μm | 0.18 μm L&S | 0.18 μm L&S |
| Exper. Exp.16 | 43 | 0.16 | Rectangular | ±0.4 μm | 0.18 μm L&S | 0.18 μm L&S |

TABLE 12

| | Dose mJ/cm$^2$ | Dissolution μm L&S | Shape | Edge roughness 0.22 μm L&S |
|---|---|---|---|---|
| Exper. Exp. 11 | 42 | 0.21 | Rectangular | 12 nm |
| Exper. Exp. 12 | 45 | 0.21 | Rectangular | 16 nm |
| Exper. Exp. 13 | 46 | 0.21 | Rectangular | 21 nm |
| Exper. Exp. 14 | 50 | 0.21 | Rectangular | 13 nm |
| Exper. Exp. 15 | 57 | 0.22 | Rectangular | 10 nm |
| Exper. Exp. 16 | 63 | 0.21 | Rectangular | 10 nm |

Reference Examples 1 to 5

Mixed solutions comprising the components of the following Table 13 were filtered with the use of a filter of 0.1 μm mesh to prepare chemically amplified resist compositions. The acid generator obtained in Reference Example 3 and in Reference Example 4 was not respectively dissolved in a propyleneglycol monomethyl ether acetate solution, so that resists were not prepared. Thus, in Reference Examples 3 and 5, δ-butyrolactone was used as a dissolving auxiliary.

TABLE 13

| | | |
|---|---|---|
| Ref. Exp. 1 | Poly(p-1-ethoxyethoxystyrene/p-tert-butoxycarbonyloxystyrene/p-hydroxystyrene) [Mw 20000; Mw/Mn 1.12] | 6.0 g |
| | b is (cyclohexylsulfonyl) diazomethane | 0.2 g |
| | diphenyl-p-methylphenyl sulfonium p-toluene sulfonate [compound of Comparative Example 1] | 0.1 g |
| | tri-n-butylamine | 0.1 g |
| | fluorine-containing nonionic surfactant [commercially available product] | 0.1 g |
| | propyleneglycol monomethyl ether acetate | 28.5 g |
| Ref. Exp. 2 | Poly(p-1-ethoxyethoxystyrene/p-tert-butoxycarbonyloxystyrene/p-hydroxystyrene) [Mw 20000; Mw/Mn 1.12] | 6.0 g |
| | b is (cyclohexylsulfonyl) diazomethane | 0.2 g |
| | diphenyl-p-methylphenyl sulfonium p-toluene sulfonate [compound of Comparative Example 2] | 0.1 g |
| | tri-n-butylamine | 0.1 g |
| | fluorine-containing nonionic surfactant [commercially available product] | 0.1 g |
| | propyleneglycol monomethyl ether acetate | 28.5 g |
| Ref. Exp. 3 | Poly(p-1-ethoxyethoxystyrene/p-tert-butoxycarbonyloxystyrene/p-hydroxystyrene) [Mw 20000; Mw/Mn 1.12] | 6.0 g |
| | b is (cyclohexylsulfonyl) diazomethane | 0.2 g |
| | diphenyl-m-tert-butoxyphenyl sulfonium p-toluene sulfonate [compound of Comparative Example 3] | 0.1 g |
| | tri-n-butylamine | 0.1 g |
| | δ-butyrolactone | 0.5 g |
| | fluorine-containing nonionic surfactant [commercially available product] | 0.1 g |
| | propyleneglycol monomethyl ether acetate | 28.0 g |
| Ref. Exp. 4 | Poly(p-1-ethoxyethoxystyrene/p-pivaloyloxystyrene/p-hydroxystyrene) [Mw 20000; Mw/Mn 1.15] | 6.0 g |
| | b is (cyclohexylsulfonyl) diazomethane | 0.2 g |
| | diphenyl-p-methylphenyl sulfonium p-toluene sulfonate [compound of Comparative Example 1] | 0.1 g |
| | dicyclohexylmethylamine | 0.1 g |
| | fluorine-containing nonionic surfactant [commercially available product] | 0.1 g |
| | propyleneglycol monomethyl ether acetate | 29.0 g |
| Ref. Exp. 5 | Poly(p-1-ethoxyethoxystyrene/p-tert-butoxycarbonyloxystyrene/p-hydroxystyrene) [Mw 20000; Mw/Mn 1.12] | 6.0 g |
| | b is (cyclohexylsulfonyl) diazomethane | 0.2 g |
| | diphenyl-2,4,6-trimethylphenylsulfonium 2,4,6-trimethoxybenzene sulfonate [compound of Comparative Example 4] | 0.1 g |
| | tri-n-butylamine | 0.1 g |
| | δ-butyrolactone | 0.5 g |
| | fluorine-containing nonionic surfactant [commercially available product] | 0.1 g |
| | propyleneglycol monomethyl ether acetate | 28.5 g |

On the above resist compositions, measurement of the number of fine particles was conducted at predetermined timing under storage at 23° C. after the same manner as described in Experimental Example 1. The result is shown in Table 14.

TABLE 14

| Storage day | 0 day | 3 days | 1 week | 2 weeks | 1 month | 2 months | 3 months | 6 months |
|---|---|---|---|---|---|---|---|---|
| Ref. Exp. 1 | ≦10 | 1000 | 9000 | 9000 | 8800 | 8770 | 8750 | 8750 |
| Ref. Exp. 2 | ≦10 | ≦10 | 15 | 30 | 100 | 250 | 1700 | 6550 |
| Ref. Exp. 3 | ≦10 | ≦10 | 8550 | 9000 | 9000 | 8800 | 8800 | 8800 |
| Ref. Exp. 4 | ≦10 | 1500 | 8500 | 8800 | 8800 | 8750 | 8700 | 8800 |
| Ref. Exp. 5 | ≦10 | ≦10 | 8550 | 8800 | 8800 | 8750 | 8750 | 8750 |

*unit: number/ml
particle size ≧0.2 μm

Further, patterns were formed with the use of the above resist composition solutions after the same manner as described in Experimental Example 1. The result on an anti-reflective film is shown in Table 15 and the result on a silicone wafer is shown in Table 16.

TABLE 15

| | Dose mJ/cm$^2$ | Dissolution μm L&S | Shape | DOF 0.20 μm L&S | Delay time 0 minute | After 2 hours |
|---|---|---|---|---|---|---|
| Ref. Exp. 1 | 30 | 0.16 | Rectangular | ±0.4 μm | 0.18 μm L&S | 0.18 μm L&S |
| Ref. Exp. 2 | 30 | 0.16 | Rectangular | ±0.4 μm | 0.18 μm L&S | 0.18 μm L&S |
| Ref. Exp. 3 | 31 | 0.16 | Rectangular | ±0.4 μm | 0.18 μm L&S | 0.18 μm L&S |
| Ref. Exp. 4 | 32 | 0.16 | Rectangular | ±0.4 μm | 0.18 μm L&S | 0.18 μm L&S |
| Ref. Exp. 5 | 40 | 0.16 | Rectangular | ±0.4 μm | 0.18 μm L&S | 0.18 μm L&S |

TABLE 16

| | Dose mJ/cm$^2$ | Dissolution μm L&S | Shape | Edge roughness 0.22 μm L&S |
|---|---|---|---|---|
| Ref. Exp. 1 | 45 | 0.21 | Rectangular | 32 nm |
| Ref. Exp. 2 | 45 | 0.21 | Rectangular | 33 nm |
| Ref. Exp. 3 | 46 | 0.21 | Rectangular | 30 nm |
| Ref. Exp. 4 | 48.5 | 0.21 | Rectangular | 33 nm |
| Ref. Exp. 5 | 60 | 0.22 | Rectangular | 30 nm |

Reference Examples 6 to 8

Mixed solutions comprising the components of the following Table 17 were filtered with the use of a filter of 0.1 μm mesh to prepare chemically amplified resist compositions.

TABLE 17

| | | |
|---|---|---|
| Ref. Exp. 6 | Poly (p-1 -ethoxyethoxystyrene/p-tert-butoxycarbonyloxystyrene/p-hydroxystyrene) [Mw 20000; Mw/Mn 1.12] | 6.0 g |
| | bis (cyclohexylsulfonyl) diazomethane | 0.2 g |
| | diphenyl-p-methylphenyl sulfonium trifluoromethane sulfonate | 0.1 g |
| | tri-n-butylamine | 0.1 g |
| | fluorine-containing nonionic surfactant (commercially available product) | 0.1 g |
| | propyleneglycol monomethyl ether acetate | 28.5 g |
| Ref. Exp. 7 | Poly (p-1-ethoxyethoxystyrene/p-tert-butoxycarbonyloxystyrene/p-hydroxystyrene) [Mw 20000; Mw/Mn 1.12] | 6.0 g |
| | bis (cyclohexylsulfonyl) diazomethane | 0.2 g |
| | diphenyl-o-methylphenyl sulfonium trifluoromethane sulfonate [intermediate compound in Example 2] | 0.1 g |
| | tri-n-butylamine | 0.1 g |
| | fluorine-containing nonionic surfactant (commercially available product) | 0.1 g |
| | propyleneglycol monomethyl ether acetate | 28.5 g |

TABLE 17-continued

| Ref. Exp. 8 | Poly (p-1-ethoxyethoxystyrene/p-pivaloyloxystyrene/p-hydroxystyrene) [Mw 20000; Mw/Mn 1.15] | 6.0 g |
| --- | --- | --- |
| | bis (cyclohexylsulfonyl) diazomethane | 0.2 g |
| | diphenyl-2,4,6-trimethylphenyl sulfonium trifluoromethane sulfonate | 0.1 g |
| | dicyclohexylmethylamine | 0.1 g |
| | fluorine-containing nonionic surfactant (commercially available product) | 0.1 g |
| | propyleneglycol monomethyl ether acetate | 29.0 g |

Patterns were formed with the use of the above resist composition solutions after the same manner as described in Experimental Example 1. The result on an antireflective film is shown in Table 18 and the result on a silicone wafer is shown in Table 19.

TABLE 18

| | Dose | Dissolution | | DOF 0.20 μm | Delay time | |
| --- | --- | --- | --- | --- | --- | --- |
| | mJ/cm² | μm L&S | Shape | L&S | 0 minute | After 2 hours |
| Ref. Exp.6 | 21 | 0.16 | Taper | ±0.4 μm | 0.18 μm L&S | 0.15 μm L&S |
| Ref. Exp.7 | 21 | 0.16 | Taper | ±0.4 μm | 0.18 μm L&S | 0.15 μm L&S |
| Ref. Exp.8 | 23 | 0.16 | Taper | ±0.4 μm | 0.18 μm L&S | 0.15 μm L&S |

TABLE 19

| | Dose mJ/cm² | Dissolution μm L&S | Shape | Edge roughness 0.22 μm L&S |
| --- | --- | --- | --- | --- |
| Ref. Exp.6 | 30 | 0.21 | Taper | 55 nm |
| Ref. Exp.7 | 32 | 0.21 | Taper | 50 nm |
| Ref. Exp.8 | 34 | 0.21 | Slightly Taper | 55 nm |

As clear from the comparison between the result shown in Table 4, 6 and 10 and the result shown in Table 14, use of known sulfonium salts as a acid generator for a resist caused rapid increase of the number of fine particles during storage period (Table 14), but use of the sulfonium salt compound of the present invention shown by the general formula [1] of [3] caused no rapid increase of the number of fine particles (Table 4, 6 and 10).

Further, as clear from the comparison between the result shown in Table 7, 8, 11, 12, 18 and 19 and the result shown in Table 15 and 16, use of sulfonium salt compound of the present invention (co-use with a specific diazodisulfone compound) attained the same ability of sensitivity, resolution, DOF, PED, etc. as using known sulfonium salts.

Still, further, it is understood that use of the sulfonium salt compound of the present invention as an acid generator has no drawback such as patterns having large edge roughness observed in the case of use of known acid generators and can form patterns having rectangular shape and small edge roughness.

Experimental Example 17

Cationic Photo Polymerization

In 25 ml of methylene chloride were dissolved 25 g of isobutylvinyl ether and 5 g of diphenyl-2,4,6-trimethylphenylsulfonium p-toluenesulfonate under nitrogen stream, and the resultant was cooled to 0° C. and irradiated with a high pressure mercury lump (HL-100 type; mfd. by Fuji Glass Works) for 12 hours.

The resultant was diluted by addition of 40 ml of methylene chloride and poured into 500 ml of methanol to give precipitates. The precipitated polymer was recovered by filtration and dried under reduced pressure to give 0.7 g of poly (isobutylvinyl ether) of Mw 3700 and Mw/Mn 2.21.

EFFECT OF INVENTION

The sulfonium salt compound of the present invention can generate an acid by irradiation with UV, deep UV, KrF excimer laser, ArF excimer laser, $F_2$ excimer laser, electron beams, X-ray or actinic rays, and therefore the sulfonium salt can be used as an acid generator, which can form a good pattern without being accompanied with drawback such as formation of fine particles during storage, which is observed in case of use of known acid generator, Further, the sulfonium salt compound is useful as an acid generator for resists and also useful as a cationic photo polymerization initiator.

What is claimed is:

1. A triphenyl sulfonium salt compound shown by the general formula [1] or [3]:

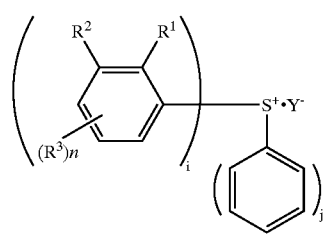

[1]

(wherein $R^1$ and $R^2$ are each independently a hydrogen atom or a lower alkyl group, provided that at least one of $R^1$ and $R^2$ are a lower alkyl group, $R^3$s are each independently an alkyl group, n is an integer of 0 to 3, i is an integer of 1 to 3, j is an integer of 0 to 2, provided that i+j=3, Y⁻ is an anion derived from a sulfonic acid shown by the general formula [2]

 [2]

[wherein R⁴ is an alkyl group or an aryl group which may have as a substituent an alkyl group]),

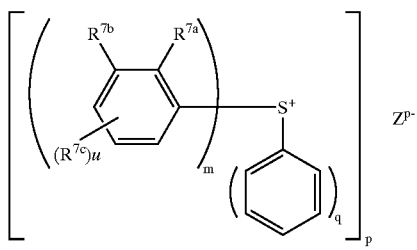

(wherein $R^{7a}$ and $R^{7b}$ are each independently a hydrogen atom or an alkyl group which may have a substituent, provided that at least one of $R^{7a}$ and $R^{7b}$ are an alkyl group which may have a substituent, $R^{7c}$s are each independently an alkyl group which may have a substituent, u is an integer of 0 to 3, m is an integer of 1 to 3, q is an integer of 0 to 2, provided that m+q=3, p is 1 or 2 and $Z^{p-}$ is an anion derived from a carboxylic acid).

2. A compound shown by the general formula [1]

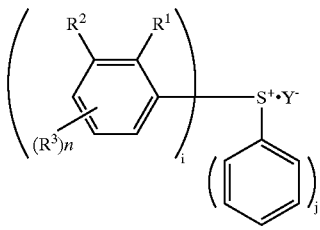

(wherein $R^1$ and $R^2$ are each independently a hydrogen atom or a lower alkyl group, provided that at least one of $R^1$ and $R^2$ are a lower alkyl group, $R^3$s are each independently an alkyl group, n is an integer of 0 to 3, i is an integer of 1 to 3, j is an integer of 0 to 2, provided that i+j=3, Y⁻ is an anion derived from a sulfonic acid shown by the general formula [2]

 [2]

[wherein R⁴ is an alkyl group or an aryl group which may have as a substituent an alkyl group]).

3. A compound shown by the general formula [3]

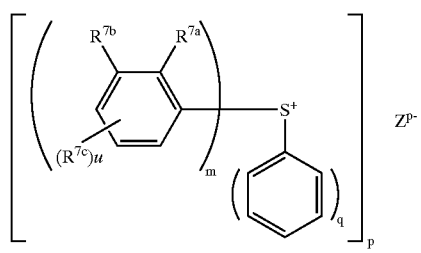

(wherein $R^{7a}$ and $R^{7b}$ are each independently a hydrogen atom or an alkyl group which may have a substituent, provided that at least one of $R^{7a}$ and $R^{7b}$ are an alkyl group which may have a substituent, $R^{7c}$s are each independently an alkyl group which may have a substituent, u is an integer of 0 to 3, m is an integer of 1 to 3, q is an integer of 0 to 2, provided that m+q=3, p is 1 or 2 and $Z^{p-}$ is an anion derived firom a carboxylic acid).

4. A compound according to claim 3, wherein the carboxylic acid is a compound shown by the general formula [4] or [5]

 [4]

(wherein $R^5$ is a hydrogen atom or a monovalent hydrocarbon group which may have a substituent),

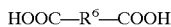 [5]

(wherein $R^6$ is a direct-linkage or a divalent hydrocarbon residue which may have a substituent).

5. A compound according to claim 2, wherein $R^1$ is a lower alkyl group and $R^2$ is a hydrogen atom.

6. A compound according to claim 5, wherein the lower alkyl group is a methyl group or an ethyl group.

7. A compound according to claim 6, wherein n is 0.

8. A compound according to claim 5, wherein $R^3$ is an alkyl group having 1 to 10 carbon atoms.

9. A compound according to claim 2, wherein a partial structure in the general formula [1]

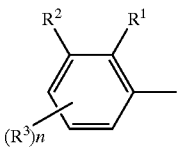

is an o-methylphenyl group, a m-methylphenyl group, a 2,3-dirnethylphenyl group, an o-ethylphenyl group, a m-ethylphenyl group, a 2,3-diethylphenyl group, a 2,4-dimethylphenyl group, a 3,4-dimethylphenyl group, a 2,6-dimethylphenyl group, a 3,5-dimethylphenyl group, a 2,4,6-trimethylphenyl group, a 3,4,5-trimethylphenyl group.

10. A compound according to claim 2, wherein $R^4$ is an alkyl group having 1 to 20 carbon atoms, a phenyl group or a naphthyl group.

11. A compound according to claim 2, wherein $R^4$ is a phenyl group having an alkyl group having 1 to 10 carbon atoms as 1 to 3 substituents.

12. A compound according to claim 11, wherein $R^4$ is a 4-methylphenyl group.

13. A compound according to claim 3, wherein alkyl group in the alkyl group which may have a substituent, shown by $R^{7a}$, $R^{7b}$ and $R^{7c}$ is an alkyl group having 1 to 6 carbon atoms.

14. A compound according to claim 4, wherein the monovalent hydrocarbon residue shown by $R^5$ is an alkyl group having 1 to 20 carbon atoms.

15. A compound according to claim 4, wherein the monovalent hydrocarbon residue shown by $R^5$ is a phenyl group or a naphthyl group.

16. A compound according to claim 14, wherein the substituent in the monovalent hydrocarbon residue is a halogen atom, a lower alkyl group, a lower haloalkyl group or a nitro group.

17. A compound according to claim 15, wherein the substituent in the monovalent hydrocarbon residue is a halogen atom, a lower alkyl group, a lower haloalkyl group or a nitro group.

18. A compound according to claim 4, wherein the dialent hydrocabon residue shown by $R^6$ is an alkylene group having 1 to 10 carbon atoms or an alkenylene group having 2 to 10 carbon atoms.

19. A compound according to claim 4, wherein the divalent hydrocarbon residue shown by $R^6$ is a phenylene group or a naphthylene group.

20. A compound according to claim 18, wherein the substituent in the divalent hydrocarbon residue is a halogen atom, a lower alkyl group, a lower haloalkyl group or nitro group.

21. A compound according to claim 19, wherein the substituent in the divalent hydrocarbon residue is a halogen atom, a lower alkyl group, a lower haloalkyl group or nitro group.

22. A compound according to claim 2, wherein the compound shown by the general formula [1] is diphenyl-2,4,6-trimethylphenylsulfonium p-toluenesulfonate or diphenyl-2,4,6-trimethylphenylsulfonium 1-octanesulfonate.

23. A compound according to claim 3, wherein the compound shown by the general formula [3] is diphenyl-2,4,6-trimethylphenylsulfonium 1-perfluorooctanoate or diphenyl-2,4,6-trimethylphenylsulfonium p-trifluoromethylbenzoate.

24. An acid generator for a chemically amplified resist, which comprising the compound in claim 1.

25. An acid generator composition for a chemically amplified resist, which comprising the compound in claim 1 and a diazodisulfone compound.

26. A resist composition, which comprising a polymer containing as pending group a protecting group which becomes soluble in an alkaline developing solution by an act of an acid and the compound in claim 1.

27. A resist composition, which comprising a polymer soluble in an alkaline developing solution, a dissolving-inhibiting agent containing as pending group a protecting group which becomes soluble in an alkaline developing solution by an act of an acid and the compound in claim 1.

28. A resist composition, which comprising a polymer soluble in an alkaline developing solution, a cross-linking agent which cross-links the polymer to make it insoluble in an alkaline developing solution by treatment under heating in the presence of an acid and the compound in claim 1.

29. A resist composition according to claim 26, wherein the polymer containing as pending group a protecting group which becomes soluble in an alkaline developing solution by an act of an acid is one shown by the general formula [9]

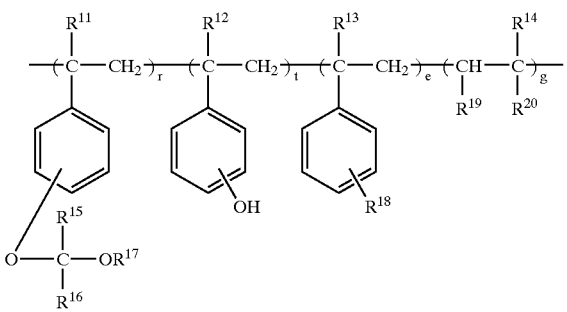

[9]

(wherein $R^{11}$, $R^{12}$, $R^{13}$ and $R^{14}$ are each independently a hydrogen atom or a methyl group, $R^{15}$ is a hydrogen atom or a lower alkyl group, $R^{16}$ is a lower alkyl group, and $R^{15}$ and $R^{16}$ may form an alicyclic ring together with a carbon atom to which they are bound, $R^{17}$ is an alkyl group or an aralkyl group, $R^{18}$ is a hydrogen atom, a lower alkyl group, a lower alkoxy group, a tetrahydropyranyloxy group, a tetrahydrofuranyloxy group, a tert-butoxycarbonyloxy group, a tert-amyloxycarbonyloxy group, a benzoyloxy group, an acetyloxy group, a pivaloyloxy group or a tert-butoxycarbonylmethyloxy group, $R^{19}$ is a hydrogen atom or a cyano group, $R^{20}$ is a cyano group or a carboxyl group which may be esterified, r, e and g are 0 or a natural number and t is a natural number, providing that $0 \leq r/r+t+e+g \leq 0.5$, $0 \leq e/r+t+e+g \leq 0.3$, $0 \leq g/r+t+e+g \leq 0.3$ and $0.2 < r+e+g/r+t+e+g \leq 0.8$).

30. A resist composition according to claim 27, wherein the polymer soluble in an alkaline developing solution is one shown by the general formula [10]

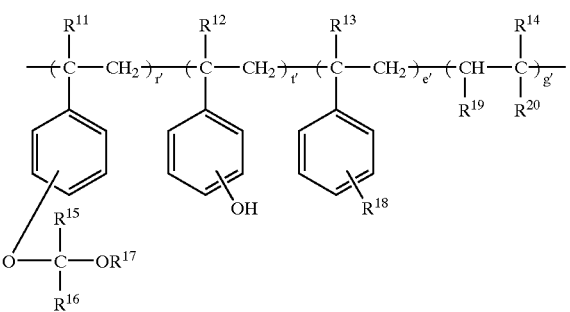

[10]

(wherein $R^{11}$, $R^{12}$, $R^{13}$ and $R^{14}$ are each independently a hydrogen atom or a methyl group, $R^{15}$ is a hydrogen atom or a lower alkyl group, $R^{16}$ is a lower alkyl group, and $R^{15}$ and $R^{16}$ may form an alicyclic ring together with a carbon atom to which they are bound, $R^{17}$ is an alkyl group or an aralkyl group, $R^{18}$ is a hydrogen atom, a lower alkyl group, a lower alkoxy group, a tetrahydropyranyloxy group, a tetrahydrofuranyloxy group, a tert-butoxycarbonyloxy group, a tert-amyloxycarbonyloxy group, a benzoyloxy group, an acetyloxy group, a pivaloyloxy group or a tert-butoxycarbonylmethyloxy group, $R^{19}$ is a hydrogen atom or a cyano group, $R^{20}$ is a cyano group or a carboxyl group which may be esterified, r', e' and g' are 0 or a natural number, t' is a natural number, providing that $0 \leq r'/r'+t'+e'+g' \leq 0.2$, $0 \leq e'/r'+t'+e'+g' \leq 0.2$, $0 \leq g'/r'+t'+e'+g' \leq 0.2$ and $0 \leq r'+e'+g'/r'+t'+e'+g' \leq 0.2$).

31. A resist composition according to claim 28, wherein the polymer soluble in an alkaline developing solution is one shown by the general formula [10]

[10]

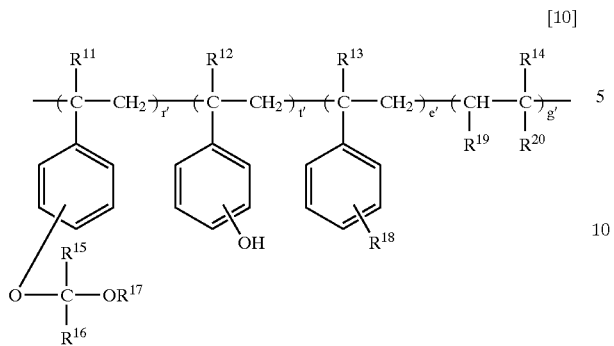

(wherein $R^{11}$, $R^{12}$, $R^{13}$ and $R^{14}$ are each independently a hydrogen atom or a methyl group, $R^{15}$ is a hydrogen atom or a lower alkyl group, $R^{16}$ is a lower alkyl group, and $R^{15}$ and $R^{16}$ may form an alicyclic ring together with a carbon atom to which they are bound, $R^{17}$ is an alkyl group or an aralkyl group, $R^{18}$ is a hydrogen atom, a lower alkyl group, a lower alkoxy group, a tetrahydropyranyloxy group, a tetrahydrofuranyloxy group, a tert-butoxycarbonyloxy group, a tert-amyloxycarbonyloxy group, a benzoyloxy group, an acetyloxy group, a pivaloyloxy group or a tert-butoxycarbonylmethyloxy group, $R^{19}$ is a hydrogen atom or a cyano group, $R^{20}$ is a cyano group or a carboxyl group which may be esterified, r', e' and g' are 0 or a natural number, t' is a natural number, providing that $0 \leq r'/r'+t'+e'+g' \leq 0.2$, $0 \leq e'/r'+t'+e'+g' \leq 0.2$, $0 \leq g'/r'+t'+e'+g' \leq 0.2$ and $0 \leq r'+e'+g'/r'+t'+e'+g' \leq 0.2$).

32. A resist composition according to claim 27, wherein the dissolving-inhibiting agent containing as a pending group a protecting group which becomes soluble in an alkaline developing solution by an act of an acid is a compound shown by the general formula [11], [12] or [13]

[11]

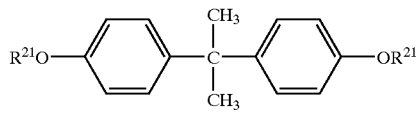

(wherein $R^{21}$s are each independently an acid labile group),

[12]

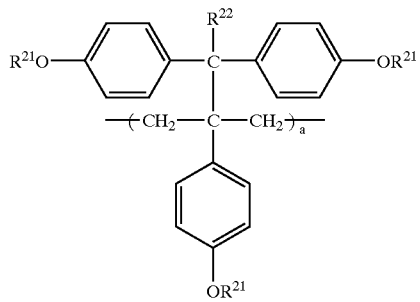

(wherein $R^{22}$ is a hydrogen atom or a methyl group, a is a natural number and $R^{21}$ has the same meaning as above),

[13]

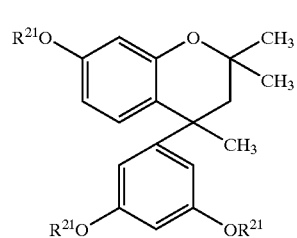

(wherein $R^{21}$ has the same meaning as above).

33. A resist composition according to claim 28, wherein the cross-linking agent which cross-links the polymer to make it insoluble in an alkaline developing solution by treatment under heating in the presence of an acid is a compound shown by the general formula [14] or [15]

[14]

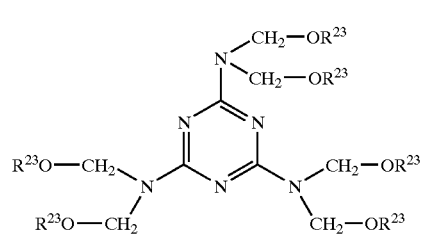

(wherein $R^{23}$s are each independently a hydrogen atom or a lower alkyl group),

[15]

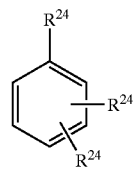

(wherein $R^{24}$s are each independently a hydrogen atom or a lower alkoxymethyl group).

34. A cationic type photo polymerization initiator, which comprising the compound in claim 1.

* * * * *